United States Patent
Golub et al.

(10) Patent No.: US 7,239,986 B2
(45) Date of Patent: Jul. 3, 2007

(54) METHODS FOR CLASSIFYING SAMPLES AND ASCERTAINING PREVIOUSLY UNKNOWN CLASSES

(75) Inventors: Todd R. Golub, Newton, MA (US);
Eric S. Lander, Cambridge, MA (US);
Jill Mesirov, Belmont, MA (US);
Donna Slonim, Somerville, MA (US);
Pablo Tamayo, Cambridge, MA (US)

(73) Assignees: Whitehead Institute for Biomedical Research, Cambridge, MA (US);
Dana-Farber Cancer Institute, Inc., Boston, MA (US)

(*) Notice: Subject to any disclaimer, the term of this patent is extended or adjusted under 35 U.S.C. 154(b) by 770 days.

(21) Appl. No.: 10/074,789

(22) Filed: Feb. 12, 2002

(65) Prior Publication Data

US 2003/0017481 A1    Jan. 23, 2003

Related U.S. Application Data

(62) Division of application No. 09/544,627, filed on Apr. 6, 2000, now Pat. No. 6,647,341.

(60) Provisional application No. 60/188,765, filed on Mar. 13, 2000, provisional application No. 60/159,477, filed on Oct. 14, 1999, provisional application No. 60/158,467, filed on Oct. 8, 1999, provisional application No. 60/135,397, filed on May 21, 1999, provisional application No. 60/128,664, filed on Apr. 9, 1999.

(51) Int. Cl.
*G06G 7/60* (2006.01)
*G06F 19/00* (2006.01)

(52) U.S. Cl. .................. 703/2; 703/11; 702/20

(58) Field of Classification Search ................. 706/20; 702/19; 514/908; 536/23.5; 703/2
See application file for complete search history.

(56) References Cited

U.S. PATENT DOCUMENTS

| | | | |
|---|---|---|---|
| 5,040,133 A | 8/1991 | Feintuch et al. | 364/581 |
| 5,179,643 A | 1/1993 | Homma et al. | 395/140 |
| 5,631,734 A | 5/1997 | Stern et al. | 356/317 |
| 5,734,796 A | 3/1998 | Pao | 395/22 |
| 5,770,722 A | 6/1998 | Lockhart et al. | 536/25.3 |
| 5,819,245 A | 10/1998 | Peterson et al. | 706/16 |
| 5,832,182 A | 11/1998 | Zhang et al. | 395/10 |
| 5,871,697 A | 2/1999 | Rothberg et al. | 422/68.1 |
| 5,925,525 A | 7/1999 | Fodor et al. | 435/6 |
| 6,760,715 B1 * | 7/2004 | Barnhill et al. | 706/16 |

FOREIGN PATENT DOCUMENTS

WO    WO 99/33982 A2    7/1999

OTHER PUBLICATIONS

Zheng et al. Reduction of breast biopsies with a modified self-organizing map. IEEE Transactions on Nerual Networks. (Nov. 1997) vol. 8, No. 6, pp. 1386-1396.*
Golub et al. Science. Oct. 15, 1999. vol. 286, pp. 531-537.*
Decaestecker et al. Journal of Neuropathology and Experimental Neurology (May, 1995) vol. 54, No. 3, pp. 371-384.*
Miyakis, et al., "Differential Expression and Mutation of the ras Family Genes in Human Breast Cancer," *Biochemical and Biophysical Research Comm.*, 251: 609-612 (1998).
Watson, M. A., et al., "Gene Expression Profiling wity Oligonucleotide Microarrays Distinguishes World Health Organization grade of Oligodendrogliomas[1]," *Cancer Research*, 61: 1825-1829 (2001).
Borrow, Julian, et al., "The t (7;11) (p15;p15) translocation in actue myeloid leukaemia fuses the genes for nucleoporin NUP98 and class I homeoprotein HOXA9," *Nature Genetics.*, 12(2): 159-167 (1996).
Buccheri, Valeria, et al., "mb-1: A New Marker for B-Lineage Lymphoblastic Leukemia," *Blood* 82(3): 853-857 (1993).
Chu, S., et al., "The Transcriptional Program of Sporulation in Budding yeast," *Science* 282: 699-705 (1998).
Cole, Kristina A., et al., "The genetics of cancer-a 3D model," *Nature Genetics* 21 38-41 (1999).
Eisen, Michael, B., et al., "Cluster analysis and display of genome-wide expression patterns," *Proc. Natl. Acad. Sci.* 95: 14863-14868 (1998).
Ermolaeva, Olga, et al., "Data management and analysis for gene expression arrays," *Nature Genetics* 20: 19-23 (1998).
Huang, Shang-Yi, et al., "Clinical, haematological and molecular studies in patients with chromosome translocation t(7;11): a study of four chinese patients in Taiwan," *British Journal of Haematology*, 96: 682-687 (1997).
Iyer, Vishwanath R., et al., "The Transcriptional Program in the Response of Human Fibroblasts to Serum," *Science* 283: 83-87 (1999).
Khan, Javed, et al., "Expression profiling in cancer using cDNA microarrays," *Electrophoresis* 20: 223-229 (1999).
Khan, Javed, et al., "Gene Expression Profiling of Alveolar Rhabdomyosarcoma with cDNA Microarrays," *Cancer Research* 58: 5009-5013 (1998).
Kononen, Juha, et al., "Tissue microarrays for high-throughput molecular profiling of tumor specimens," *Nature Medicine* 4: 844-847 (1998).
Kroon, Evert, et al., "Hoxa9 transforms primary bone marrow cells through specific collaboration with Meisla but not Pbx1b," *The EMBO Journal* 17 (13) 3714-3725 (1998).
Lander, Eric S., "The New Genomics: Global Views of Biology," *Science* 274: 536-538 (1996).
Nakamura, Takuro, et al., "Fusion of the nucleoporin gene NUP98 to HoXA9 by the chromosome translocation t(7;11) (p15;p15) in human myeloid leukaemia" *Nature Genetics* 12: 154-158 (1996).

(Continued)

*Primary Examiner*—Marjorie A. Moran
(74) *Attorney, Agent, or Firm*—Fish & Neave IP Group of Ropes & Gray LLP

(57) ABSTRACT

Methods and apparatus for classifying or predicting the classes for samples based on gene expression are described. Also described are methods and apparatus for ascertaining or discovering new, previously unknown classes based on gene expression.

12 Claims, 18 Drawing Sheets
(1 of 18 Drawing Sheet(s) Filed in Color)

OTHER PUBLICATIONS

Spellman, Paul T., et al., "Comprehensive Identification of Cell Cycle-regulated Genes of the Yeast *Saccharomyces cerevisiae* by Microarray Hybridization[D]," *Molecular Biology of the Cell* 9(12) 3273-3297 (1998).

Tamayo, Pablo, et al., "Interpreting patterns of gene experession with self-organizing maps: Methods and appliation to hematopoietic differentiation," *Proc. Natl. Acad. Sci.* 96: 2907-2912 (1999).

Tavazoie, Saeed, et al., "Systematic determination of genetic network architecture," *Nature Genetics* 22: 281-285 (1999).

Törönen, Petri, et al., "Analysis of gene expression data using self-organizing maps," *FEBS Letters* 451: 142-146 (1999).

Watson, Andrew, et al., "Technology for microarray analysis of gene expression," *Biotechnology* 9: 609-614 (1998).

Yang. George P., et al., "Combining SSH and cDNA microarrays for rapid identification of differentially expressed genes," *Nucleic Acids Research* 27(6): 1517-1523 (1999).

"Affymetrix Launches New Genome Scanning Genechip® Expression Products," [online], Sep. 1998 [retrieved on Oct. 14, 1998] . Retrieved from the Internet:<URL:http://www.affymetrix.com/press/pr980918.html.

Stipp, D., "Gene Chip Breakthrough," [online], Mar. 1997, [retrieved Oct. 15, 1998]. Retrieved from the Internet:<URL: http://www/pathfinder.com/@@NJC11CgcA1QLIOjS3/fortune/1997/970331/bio.html.

Zheng, P. et al., "Proto-oncogene PML controls genes devoted to MHC class I antigen presentation," Nature 396:373-376, (Nov. 26, 1998).

Lockhart, D.J. et al., "Expression monitoring by hybridization to high-density oligonucleotide arrays," Nature Biotechnology, 14:1675-1680, (Dec. 1998).

DeRisi, J.L. et al., "Exploring the Metabolic and Genetic Control of Gene Expression on a Genomic Scale," Science, 278:680-686, (Oct. 1997).

Lashkari, D.A. et al., "Yeast microarrays for genome wide parallel genetic and gene expression analysis," Proc. Natl. Acad. Sci. USA, 94:13057-13062 (Nov. 1997).

Miyata, Y. et al., "Phosphorylation of the immunosuppressant FK506-binding protein FKBP52 by casein kinase II: Regulation of HSP90-binding activity of FKBP52," Proc. Natl. Acad. Sci. USA, 94:14500-14505, (Dec. 1997).

Kok, K. et al., "A Gene in the chromosomal region 3p21 with greatly reduced expression in lung cancer is similar to the gene for ubiquitin-activating enzyme," Proc. Natl. Acad. Sci, USA, 90:6071-6075 (Jul. 1993).

Wodicka, L. et al., "Genome-wide expression monitoring in Saccoarmyces cerevisiae," Nature Biotechnology, 15:1359-1367 (Dec. 1997).

Jin, Y. et al., Molecular cloning of a 25-kDa high affinity rapamycin binding protein, FKBP25, J.Bio.Chem., 267(16):10942-10945, (1992).

Jobson, J.D., "Cluster Analysis" in Applied Multivariate Data Analysis, vol. II: Categorical and Multivariate Methods, (NY:Springer-Verlag) pp. 518-568 (1992).

Kohonen, T., Self-Organizing Maps, 2nd Edition, T.S. Huang et al., eds. (NY: Springer-Verlag, 1997), pp. XIII-XVIII only.

Loos, H.S. and B. Fritzke, DemoGNG (Version 1.5), [online] [Retrived Jan. 29, 1999]. Retrieved from the Internet:<URL: http://www.neuroinformatik.ruhr-uni-bochum.de/ini/VDM/research/gns/DemoGNG/GNG.html.

Kaski, S. et al., "Bibliography of Self-Organizing Map (SOM) Papers: 1981-1997," [online] Sep. 1998 [retrieved on Mar. 5, 1999]. Retrieved from the Internet:<URL:http://www.icsi.berkeley.edu/~jagota/NCS.VOL1/P4_html/ vol1_4.html.

Cho, R. et al., "A genome-wide transcriptional analysis of the mitotic cell cyelc," Molecular Cell, 2:65-73 (Jul. 1998).

de Thé, H. et al., The PML-RAR Fusion mRNA Generated by the t(15;17) Translocation in Acute Promyelocytic Leukemia Encodes a Functionally Altered RAR, Cell, 66:675-684 (Aug. 1991).

Hartigan, J., "Clustering" in Clustering Algorithms, (NY:J. Wiley, 1975) pp. 1-27, 155-176.

Bamdad, C., "Surface Plasmon Resonance for Measurement of Biological Interest" in Current Protocols in Molecular Biology, (John Wiley & Sons, Inc.) pp. 20.4.1-20.4.12 (1997).

Jain, A.K. and R. C. Dubes, Algorithms for Clustering Data, (Prentice-Hall), pp. 1-27, 118-142, 262-274 (1988).

Kakizuka, A. et al., "Chromosomal translocation t(15;17) in human acute promyelocytic leukemia fuses RAR with a novel putative transcription factor, PML," Cell, 66:663-674 (Aug. 1991).

Höhfeld, J. et al., "Hip, a Novel Cochaperone Involved in the Eukaryotic Hsc70/Hsp40 Reaction Cycle," Cell, 83:589-598 (Nov. 1995).

Yoshida, H. et al., "Accelerated Degradation of PML-Retinoic Acid Receptor (PML-RARA) oncoprotein by All-trans-Retinoic Acid in Acute Promyelocytic Leukemia: Possible Role of Proteasome Pathway," Cancer Res., 56:2945-2948 (Jul. 1996).

Höhfeld, J. and S. Jentsch, GrpE-like regulation of the hsc70 chaperone by the anti-apoptotic protein BAG-1, EMBO Journal, 16 (20): 6209-6216 (1997).

Russell, L. and D. Forsdyke, "A Human Putative Lymphocyte G0/G1 Switch Gene Containing a CpG-rich Island Encodes a Small Basic Protein with the Potential to Be Phosphorylated," DNA and Cell Biol., 10(8) :581-591, (1991).

Oliva, M. et al., Promoter regulation of a differentially expressed gene in the human colonic epithelial cell lines HT29-18 and HT29-18-C1, Gene 159(1):151-157 (1995).

Beck, S. et al., "DNA Sequence Analysis of 66 kb of the Human MHC Class II Region Encoding a Cluster of Genes for Antigen Processing," J. Mol. Biol. 228:433-441 (Nov. 1992).

"GeneChip Probe Array Synthesis," [online] Mar. 1998 [retrieved on Oct. 15, 1998]. Retrieved from the Internet: <URL: http://www.affymetrix.com/technology/ synthesis.html.

Chu, S. et al., "The Transcriptional Program of Sporulation in Budding Yeast," Science, 282, Oct. 23, 1998 (pp. 699-705).

Kalocsai, P., et al., "Visualization and analysis of Gene Expression Data," Journal of the Association for Laboratory Automation 4(5): 58-61 (1999).

Shiosaka, T. and Tanaka, Y., "Expression of Selected Genes and Oncogenes in Differentiated HL-60 Cells and Primary Cells from Human Leukemias," *Anticancer Research*, 9:1249-1264 (1989).

Ben-Dor, A., et al., "Tissue Classification with Gene Expression Profiles," *Journal of Computational Biology*, 7(3/4) 559-583 (2000).

Xiong, M., et al., "Computational Methods for Gene Expression-Based Tumor Classification," *Biotechniques*, 29: 1264-1270 (2000).

Dougherty, E., "Small sample issues for microarray-based classification," *Comparative and Functional Genomics*, 2: 28-34 (2001).

Park, et al., "A Nonparametric Scoring Algorithm for Indentifying Informative Genes From Microarray Data," *Pacific Symposium on Biocomputing*, pp. 52-62 (2001).

Chen, J.J. W, et al., "Profiling Expression Patterns and Isolating Differentially Expressed Genes by cDNA Microarray System with Colorimetry Detection", Genomics, vol. 51(3), pp. 313-324 (Aug. 1998).

Derisi, J. et al., "Use of a CDNA Microarray to Analyse Gene Expression Patterns in Human Cancer", Nature Genetics, vol. 11, pp. 457-460 (Dec. 1996).

Gordon, A. D., in Classification-Methods for the Exploratory Analysis of Multivariate Data, (NY:Champman and Hall) pp. 1-53 (1981).

Pennisi, E., "DNA Chips Give New View of Classic Test," Science, 283:17-18, (Jan. 1999)

Wang, K. et al., "Monitoring Gene Expression Profile Changes in Ovarian Carcinomas Using cDNA Microarray", Gene, vol. 229(1-2), pp. 101-108 (Mar. 1999).

Workman, J. L., "Gene Regulation and Cancer", Trends in Genetics, vol. 15(1) pp. 9-10 (Jan. 1999).

* cited by examiner

FIG. 10

Hierarchy of Problems in Molecular Class Prediction

| Problem: | Difficulty: | Gene Markers: | Error: | Example: | |
|---|---|---|---|---|---|
| I. Tissue or Cell Type Normal vs. Abnormal | Low | ~1000-2000 | ~0% | Normal | vs. Renal Carcinoma |
| II. Morphological Type | Low-medium | ~200-500 | ~0-5% | Leukemia ALL | vs. AML |
| III. Morphological Subtype | Medium-high | ~50-100 | ~0-15% | ALL B- | vs. T-Cell |
| IV. Treatment Outcome Drug Sensitivity | High | ~1-20 | ~5-50% | AML Treatment Outcome | |

Class Pattern
Neighborhood

Permuted Pattern
Neighborhood

CLASS PREDICTION RESULTS

| Problem Type | Biological System | Problem Distinction | Number of samples | Number of errors | Number of no calls | Number of errors (all calls) | Number of gene markers |
|---|---|---|---|---|---|---|---|
| I | Renal | Normal v. Carcinoma | 12 | 0 (0%) | 0 | 0 (0%) | >100 |
| II | Leukemia | ALL vs AML | 35 | 0 (0%) | 2 | 0 (0%) | 700 |
| III | Leukemia | ALL B v. T-Cell | 33 | 0 (0%) | 1 | 1 (3%) | 200 |
| IV | Leukemia | Treatment Outcome | 15 | 2 (13%) | 0 | 2 (13%) | 1 |

Fig. 12

METHODS FOR CLASSIFYING SAMPLES AND ASCERTAINING PREVIOUSLY UNKNOWN CLASSES

RELATED APPLICATIONS

This application is a Divisional of U.S. Utility application Ser. No. 09/544,627, filed Apr. 6, 2000 now U.S. Pat. No. 6,647,341, which claims the benefit of U.S. Provisional Application No. 60/188,765, filed Mar. 13, 2000; U.S. Provisional Application No. 60/159,477, filed on Oct. 14, 1999; U.S. Provisional Application No. 60/158,467, filed on Oct. 8, 1999; U.S. Provisional Application No. 60/135,397, filed May 21, 1999; and U.S. Provisional Application No. 60/128,664, filed Apr. 9, 1999. The entire teachings of the above applications are incorporated herein by reference.

BACKGROUND OF THE INVENTION

Classification of biological samples from individuals is not an exact science. In many instances, accurate diagnosis and safe and effective treatment of a disorder depends on being able to discern biological distinctions among morphologically similar samples, such as tumor samples. The classification of a sample from an individual into particular disease classes has typically been difficult and often incorrect or inconclusive. Using traditional methods, such as histochemical analyses, immunophenotyping and cytogenetic analyses, often only one or two characteristics of the sample are analyzed to determine the sample's classification, resulting in inconsistent and sometimes inaccurate results. Such results can lead to incorrect diagnoses and potentially ineffective or harmful treatment.

For example, acute leukemia was first successfully treated by Farber and colleagues in the 1940's, and it was recognized that treatment responses were variable (Farber, et al, *NEJM* 238:787–793 (1948)). Subtle differences in nuclear shape and granularity were suggestive of distinct subtypes of acute leukemia, but such morphological distinctions were difficult to reproduce (C. E. Forkner, *Leukemia and Allied Disorders*, (New York, Macmillan) (1938); E. Frei et al., *Blood* 18:431–54 (1961); Medical Research Council, *Br Med J* 1:7–14 (1963)). By the 1960s, these distinctions were further strengthened by enzyme-based histochemical analyses which demonstrated that some leukemias were periodic-acid-schiff (PAS) positive, whereas others were myeloperoxidase positive. This was the basis of the first attempts to classify the acute leukemias into those arising from lymphoid precursors (acute lymphoblastic leukemia, ALL) and those arising from myeloid precursors (acute myeloid leukemia, AML). This classification was further solidified by the development in the 1970s of antibodies recognizing either lymphoid or myeloid cell surface molecules. Most recently, particular subtypes of acute leukemia have been found to be associated with specific chromosomal translocations; for example, the t(12;21)(p13;q22) translocation occurs in 25% of patients with ALL, whereas the t(8;21) (q22;q22) occurs in 15% of patients with AML.

No single test is currently sufficient to establish the diagnosis of AML vs. ALL. Rather, current clinical practice involves an experienced hematopathologist's interpretation of the tumor's morphology, histochemistry, immunophenotyping and cytogenetic analysis, each of which is performed in a separate, highly specialized laboratory. Correct distinction of ALL from AML is critical for successful treatment: chemotherapy regimens for ALL generally contain corticosteroids, vincristine, methotrexate, and L-asparaginase, whereas most AML regimens rely on a backbone of daunorubicin and cytarabine. While remissions can be achieved using ALL therapy for AML (and vice versa), cure rates are markedly diminished, and unwarranted toxicities are encountered. Thus, the ability to accurately classify a biological sample as an AML sample or an ALL sample is quite important.

Furthermore, important biological distinctions are likely to exist which have yet to be identified due to the lack of systematic and unbiased approaches for identifying or recognizing such classes. Thus, a need exists for an accurate and efficient method for identifying biological classes and classifying samples.

SUMMARY OF THE INVENTION

The present invention relates to a method of identifying a set of informative genes whose expression correlates with a class distinction between samples, comprising sorting genes by degree to which their expression in the samples correlate with a class distinction, and determining whether said correlation is stronger than expected by chance. A gene whose expression correlates with a class distinction more strongly than expected by chance is an informative gene. A set of informative genes is identified. In one embodiment, the class distinction is a known class, and in one embodiment the class distinction is a disease class distinction. In particular, the disease class distinction can be a cancer class distinction, such as a leukemia class distinction (e.g., Acute Lymphoblastic Leukemia (ALL) or Acute Myeloid Leukemia (AML)). In another embodiment, the class distinction is a brain tumor class distinction (e.g., medulloblastoma or glioblastoma). In a further embodiment, the class distinction is a lymphoma class distinction, such as a Non-Hodgkin's lymphoma class distinction (e.g., folicular lymphoma (FL) or diffuse large B cell lymphoma (DLBCL). The known class can also be a class of individuals who respond well to chemotherapy or a class of individuals who do not response well to chemotherapy.

Sorting genes by the degree to which their expression in the sample correlates with a class distinction can be carried out by neighborhood analysis (e.g., a signal to noise routine, a Pearson correlation routine, or a Euclidean distance routine) that comprises defining an idealized expression pattern corresponding to a gene, wherein said idealized expression pattern is expression of said gene that is uniformly high in a first class and uniformly low in a second class; and determining whether there is a high density of genes having an expression pattern similar to the idealized expression pattern, as compared to an equivalent random expression pattern. The signal to noise routine is:

$$P(g,c)=(\mu_1(g)-\mu_2(g))/(\sigma_1(g)+\sigma_2(g)),$$

wherein g is the gene expression value; c is the class distinction, $\mu_1(g)$ is the mean of the expression levels for g for the first class; $\mu_2(g)$ is the mean of the expression levels for g for the second class; $\sigma_1(g)$ is the standard deviation for the first class; and $\sigma_2(g)$ is the standard deviation for the second class.

Another aspect of the present invention is a method of assigning a sample to a known or putative class, comprising determining a weighted vote of one or more informative genes (e.g., greater than 50, 100, 150) for one of the classes in the sample in accordance with a model built with a weighted voting scheme, wherein the magnitude of each vote depends on the expression level of the gene in the sample and on the degree of correlation of the gene's expression with class distinction; and summing the votes to determine the winning class. The weighted voting scheme is:

$$V_g = a_g(x_g - b_g),$$

wherein $V_g$ is the weighted vote of the gene, g; $a_g$ is the correlation between gene expression values and class distinction, P(g,c), as defined herein; $b_g = \mu_1(g) + \mu_2(g))/2$ which is the average of the mean $\log_{10}$ expression value in a first class and a second class; $x_g$ is the $\log_{10}$ gene expression value in the sample to be tested; and wherein a positive V value indicates a vote for the first class, and a negative V value indicates a negative vote for the class. A prediction strength can also be determined, wherein the sample is assigned to the winning class if the prediction strength is greater than a particular threshold, e.g., 0.3. The prediction strength is determined by:

$$(V_{win} - V_{lose})/(V_{win} + V_{lose}),$$

wherein $V_{win}$ and $V_{lose}$ are the vote totals for the winning and losing classes, respectively. When classifying a sample into an ALL disease class or an AML disease class, the informative genes can be, for example, C-myb, Proteasome iota, MB-1, Cyclin, Myosin light chain, Rb Ap48, SNF2, HkrT-1, E2A, Inducible protein, Dynein light chain, Topoisomerase II β, IRF2, TFIIEβ, Acyl-Coenzyme A, dehydrogenase, SNF2, ATPase, SRP9, MCM3, Deoxyhypusine synthase, Op 18, Rabaptin-5, Heterochromatin protein p25, IL-7 receptor, Adenosine deaminase, Fumarylacetoacetate, Zyxin, LTC4 synthase, LYN, HoxA9, CD33, Adipsin, Leptin receptor, Cystatin C, Proteoglycan 1, IL-8 precursor, Azurocidin, p62, CyP3, MCL1, ATPase, IL-8, Cathepsin D, Lectin, MAD-3, CD11c, Ebp72, Lysozyme, Properdin and/or Catalase.

The invention also encompasses a method of determining a weighted vote for an informative gene to be used in classifying a sample, comprising determining a weighted vote for one of the classes for one or more informative genes in the sample, wherein the magnitude of each vote depends on the expression level of the gene in the sample and on the degree of correlation of the gene's expression with class distinction; and summing the votes to determine the winning class. The weighted vote is determined by genes that are relevant for determining the classes, e.g., a portion or subset of the total number of informative genes.

Yet another embodiment of the present invention is a method for ascertaining a plurality of classifications from two or more samples, comprising clustering samples by gene expression values to produce putative classes; and determining whether the putative classes are valid by carrying out class prediction based on putative classes and assessing whether the class predictions have a high prediction strength. The clustering of the samples can be performed, for example, according to a self organizing map. The self organizing map is formed of a plurality of Nodes, N, and the map clusters the vectors according to a competitive learning routine. The competitive learning routine is:

$$f_{i+1}(N) = f_i(N) + \tau(d(N, N_P), i)(P - f_i(N))$$

wherein i=number of iterations, N=the node of the self organizing map, τ=learning rate, P=the subject working vector, d=distance, $N_p$=node that is mapped nearest to P, and $f_i(N)$ is the position of N at i. To determine whether the putative classes are valid the steps for building the weighted voting scheme can be carried out as described herein.

The invention also pertains to a method for classifying a sample obtained from an individual into a class (e.g., a cancer disease class such as leukemia), comprising assessing the sample for a level of gene expression for at least one gene; and, using a model built with a weighted voting scheme, classifying the sample as a function of relative gene expression level of the sample with respect to that of the model. The level of gene expression is assessed from the level of a gene product which is expressed (e.g., mRNA, tRNA, rRNA, or cRNA). Optionally, the sample can be subjected to at least one condition (e.g., time, exposure to changes in temperature, pH, or other growth/incubation conditions, exposure to an agent, such as a drug or drug candidate) and then classified.

The present invention pertains to a method, e.g., for use in a computer system, for classifying at least one sample obtained from an individual. The method comprises providing a model built by a weighted voting scheme; assessing the sample for the level of gene expression for at least one gene, to thereby obtain a gene expression value for each gene; using the model built with a weighted voting scheme, classifying the sample comprising comparing the gene expression level of the sample to the model, to thereby obtain a classification; and providing an output indication of the classification. The routines for the weighted voting scheme and neighborhood analysis are described herein. The method can be carried out using a vector that represents a series of gene expression values for the samples. The vectors are received by the computer system, and then subjected to the above steps. The methods further comprise performing cross-validation of the model. The cross-validation of the model involves eliminating or withholding a sample used to build the model; using a weighted voting routine, building a cross-validation model for classifying without the eliminated sample; and using the cross-validation model, classifying the eliminated sample into a winning class by comparing the gene expression values of the eliminated sample to level of gene expression of the cross-validation model; and determining a prediction strength of the winning class for the eliminated sample based on the cross-validation model classification of the eliminated sample. The methods can further comprise filtering out any gene expression values in the sample that exhibit an insignificant change, normalizing the gene expression value of the vectors, and/or rescaling the values. The method further comprises providing an output indicating the clusters (e.g., formed working clusters).

The invention also encompasses a method for ascertaining at least one previously unknown class (e.g., a disease class, proliferative disease class, cancer class or leukemia class) into which at least one sample to be tested is classified, wherein the sample is obtained from an individual. The method comprises obtaining gene expression levels for a plurality of genes from two or more samples; forming respective vectors of the samples, each vector being a series of gene expression values indicative of gene expression levels for the genes in a corresponding sample; and using a clustering routine, grouping vectors of the samples such that vectors indicative of similar gene expression levels are clustered together (e.g., using a self organizing map) to form working clusters, the working clusters defining at least one previously unknown class. The previously unknown class is validated by using the methods for the weighted voting scheme described herein. The self organizing map is formed of a plurality of Nodes, N, and clusters the vectors according to a competitive learning routine. The competitive learning routine is:

$$f_{i+1}(N) = f_i(N) + \tau(d(N, N_P), i)(P - f_i(N))$$

wherein i=number of iterations, N=the node of the self organizing map, τ=learning rate, P=the subject working vector, d=distance, $N_p$=node that is mapped nearest to P, and $f_i(N)$ is the position of N at i.

The invention also pertains to a computer apparatus for classifying a sample into a class, wherein the sample is obtained from an individual, wherein the apparatus comprises: a source of gene expression values of the sample; a processor routine executed by a digital processor, coupled to receive the gene expression values from the source, the processor routine determining classification of the sample by comparing the gene expression values of the sample to a model built with a weighted voting scheme; and an output assembly, coupled to the digital processor, for providing an indication of the classification of the sample. The model is built with a weighted voting scheme, as described herein. The output assembly can comprises a display of the classification.

Yet another embodiment is a computer apparatus for constructing a model for classifying at least one sample to be tested having a gene expression product, wherein the apparatus comprises a source of vectors for gene expression values from two or more samples belonging to two or more classes, the vector being a series of gene expression values for the samples; a processor routine executed by a digital processor, coupled to receive the gene expression values of the vectors from the source, the processor routine determining relevant genes for classifying the sample, and constructing the model with a portion of the relevant genes by utilizing a weighted voting scheme. The apparatus can further include a filter, coupled between the source and the processor routine, for filtering out any of the gene expression values in a sample that exhibit an insignificant change; or a normalizer, coupled to the filter, for normalizing the gene expression values. The output assembly can be a graphical representation. The graphical representation can be color coordinated with shades of contiguous colors (e.g., blue, red, etc.).

The invention also involves a machine readable computer assembly for classifying a sample into a class, wherein the sample is obtained from an individual, wherein the computer assembly comprises a source of gene expression values of the sample; a processor routine executed by a digital processor, coupled to receive the gene expression values from the source, the processor routine determining classification of the sample by comparing the gene expression values of the sample to a model built with a weighted voting scheme; and an output assembly, coupled to the digital processor, for providing an indication of the classification of the sample. The invention also includes a machine readable computer assembly for constructing a model for classifying at least one sample to be tested having a gene expression product, wherein the computer assembly comprises a source of vectors for gene expression values from two or more samples belonging to two or more classes, the vector being a series of gene expression values for the samples; a processor routine executed by a digital processor, coupled to receive the gene expression values of the vectors from the source, the processor routine determining relevant genes for classifying the sample, and constructing the model with a portion of the relevant genes by utilizing a weighted voting scheme.

In one embodiment, the invention includes a method of determining a treatment plan for an individual having a disease, comprising obtaining a sample from the individual; assessing the sample for the level of gene expression for at least one gene; using a computer model built with a weighted voting scheme, classifying the sample into a disease class, as a function of relative gene expression level of the sample with respect to that of the model; and using the disease class, determining a treatment plan. Another application is a method of diagnosing or aiding in the diagnosis of an individual, wherein a sample from the individual is obtained, comprising assessing the sample for the level of gene expression for at least one gene; and using a computer model built with a weighted voting scheme, classifying the sample into a class of the disease including evaluating the gene expression level of the sample with respect to gene expression level of the model; and diagnosing or aiding in the diagnosis of the individual. The invention also pertains to a method for determining a drug target of a condition or disease of interest (e.g., genes that are relevant/important for a particular class), comprising assessing a sample obtained from an individual for the level of gene expression for at least one gene; and using a neighborhood analysis routine, determining genes that are relevant for classification of the sample, to thereby ascertain one or more drug targets relevant to the classification. The invention also includes a method for determining the efficacy of a drug designed to treat a disease class, comprising obtaining a sample from an individual having the disease class; subjecting the sample to the drug; assessing the drug-exposed sample for the level of gene expression for at least one gene; and, using a computer model built with a weighted voting scheme, classifying the drug-exposed sample into a class of the disease as a function of relative gene expression level of the sample with respect to that of the model. Another method for determining the efficacy of a drug designed to treat a disease class, wherein an individual has been subjected to the drug, comprises obtaining a sample from the individual subjected to the drug; assessing the sample for the level of gene expression for at least one gene; and using a model built with a weighted voting scheme, classifying the sample into a class of the disease including evaluating the gene expression level of the sample as compared to gene expression level of the model. Yet another application is a method of determining whether an individual belongs to a phenotypic class (e.g., intelligence, response to a treatment, length of life, likelihood of viral infection or obesity) that comprises obtaining a sample from the individual; assessing the sample for the level of gene expression for at least one gene; and using a model built with a weighted voting scheme, classifying the sample into a class of the disease including evaluating the gene expression level of the sample as compared to gene expression level of the model.

BRIEF DESCRIPTION OF THE FIGURES

The patent or application file contains at least one drawing executed in color. Copies of this patent or patent application publication with the color drawing will be provided by the Office upon request and payment of the necessary fee.

FIG. 1A is a schematic illustration of methodology of the present invention. FIG. 1B is a schematic exemplifying a neighborhood analysis. "$e_1$" denotes the expression level of the gene in $i^{th}$ sample in the initial set of samples. A class distinction is represented by an idealized expression pattern "c. " FIG. 1C is a schematic representation of the methods employed in classifying a sample.

FIG. 2A) or Acute Myeloid Leukemia (AML; FIG. 2B).

FIG. 3A is a graph showing the Prediction Strengths (PS) for the samples in cross-validation (left) and on the independent sample (right). Median PS is denoted by a horizontal line. Predictions with PS below 0.3 are considered uncertain. FIG. 3B is a graph showing genes that distinguish ALL samples from AML samples.

FIG. 5A is a schematic representation of a 2-cluster Self Organizing Map (SOM) performed with a 2×1 grid to ascertain ALL and AML classifications. FIG. 5B is a graph of scatterplots showing the PS distributions for class predictors. The first two plots show the distribution for the predictor created to classify samples as 'A1-type' or 'A2-type' tested in cross-validation on the initial dataset (median PS=0.86) and on the independent dataset (median PS=0.61). The remaining plots show the distribution for two predictors corresponding to random classes. FIG. 5C is a schematic representation of a 4-cluster SOM. AML samples are shown as black circles, T-lineage ALL as striped squares, and B-lineage ALL as grey squares. T- and B-lineages were differentiated on the basis of cell-surface immunophenotyping. The classes were designated as B1, B2, B3 and B4. FIG. 5D is a graphical representation of the PS distributions for pairwise comparison among classes B1, B2, B3 and B4.

FIG. 10 is an illustration showing the hierarchy of problems (Tissue or Cell Type, Normal vs. Abnormal; Morphological Type; Morphological Subtype; and Treatment Outcome and Drug Sensitivity) in molecular class prediction.

FIG. 12 is a table showing the class prediction results for various problems types (Normal vs. Carcinoma; ALL vs. AML; ALL B-cell vs. T-cell; and Treatment Outcome).

DETAILED DESCRIPTION OF THE INVENTION

Figure 1A:
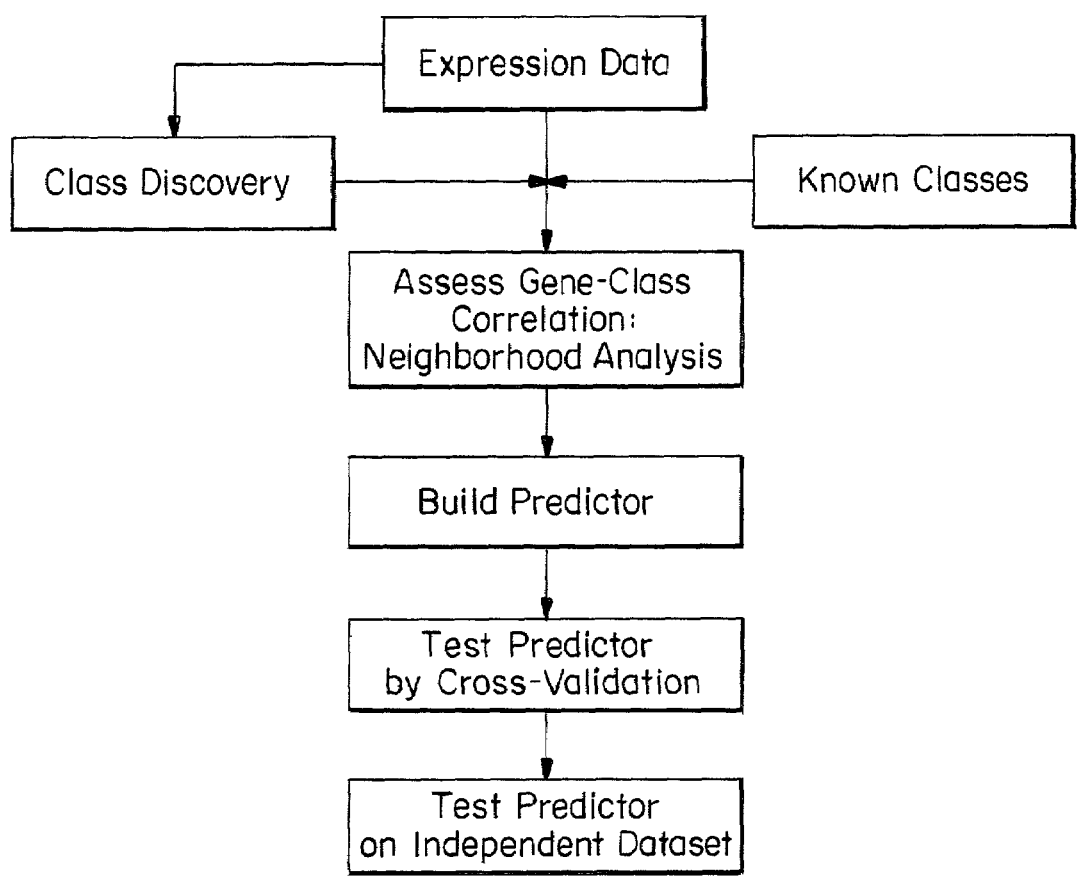
FIGS. 1A–1C are schematic diagrams which illustrate embodiments of the invention.

The present invention relates to methods and apparatus for classifying a sample using gene expression levels in the sample. The methods involve assessing the sample for the level of gene expression for at least one gene and classifying the sample using a weighted voting scheme. The weighted voting scheme advantageously allows for the classification of a sample on the basis of multiple gene expression values.

Until now, it has been difficult to assess the genetic information provided by a sample because genetic information can be provided for thousands for genes simultaneously. However, the present invention allows efficient and effective analysis of relevant genetic information and classification of a sample.

Sample classification (e.g., classifying a sample) can be performed for many reasons. For example, it may be desirable to classify a sample from an individual for any number of purposes, such as to determine whether the individual has a disease of a particular class or type so that the individual can obtain appropriate treatment. Other reasons for classifying a sample include predicting treatment response (e.g., response to a particular drug or therapy regimen) and predicting phenotype (e.g., the likelihood of viral infection or obesity). Thus, the applications of the invention are numerous and are not limited to the specific examples described herein. The invention can be used in a variety of applications to classify samples based on the patterns of gene expression of one or more genes in the sample.

For example, cancer is a disease for which several classes or types exist, many requiring different treatments. Cancer is not a single disease, but rather a family of disorders arising from distinct cell types by distinct pathogenetic mechanisms. The challenge of cancer treatment has been to target specific therapies to particular tumor types, to maximize effectiveness and to minimize toxicity. Improvements in cancer classification have thus been central to advances in cancer treatment.

Cancer classification has been based primarily on the morphological appearance of the tumor. Distinct therapeutic approaches have thus been fashioned for tumors of different organs (for example, breast vs. lung) or different cell types within an organ (for example, Hodgkin's vs. non-Hodgkin's lymphoma). Classification by morphology alone, however, has serious limitations. Tumors with similar histopathological appearance can follow significantly different clinical courses and show different responses to therapies.

For example, the "small round blue cell tumor" (SRBCT), has been subclassified using cytogenetic and immunohistochemical analysis into a number of biologically distinct subgroups, including neuroblastoma, rhabdomyosarcoma, and Ewing's sarcoma (C. F. Stephenson, et al, *Hum Pathol* 23:1270–7 (1992); O. Delattre, et al., *N Engl J Med* 331: 294–9 (1994); C. Turc-Carel, et al., *Cancer Genet Cytogenet* 19:361–2 (1986); E. C. Douglass, et al., *Cytogenet Cell Genet* 45:148–55 (1987); R. Dalla-Favera, et al., *Proc Natl Acad Sci USA* 79:7824–7 (1982); R. Taub, et al., *Proc Natl Acad Sci USA* 79:7837–41 (1982); G. Balaban-Malenbaum, F. Gilbert, *Science* 198:739–41 (1977)). Each subgroup has a distinct clinical course and therapeutic approach aimed at maximizing cure rates and minimizing treatment-related side effects. Other prominent examples of subclassifications with major therapeutic consequences include the subclassification of leukemias and lymphomas.

For many more tumors and other disorders, important subclasses are likely to exist but have yet to be defined by molecular markers. For example, prostate cancers of identical grade (based on morphological criteria) can have widely variable clinical courses ranging from indolent growth over decades to explosive growth resulting in rapid patient death. Thus, sample classification, which has historically relied on specific biological insights, would be greatly improved by the availability of systematic and unbiased approaches for recognizing subclasses; the present invention provides such an approach.

In one embodiment, the present invention was used to classify samples from individuals having leukemia as being either AML samples or ALL samples. Although the distinction between AML and ALL has been well established, class prediction of individual leukemia cases remains a complicated process. The present invention has been shown, as described herein, to accurately and reproducibly distinguish AML samples from ALL samples, and to correctly classify new samples as belonging to one or the other of these classes. The invention has also been shown to accurately predict the distinction between two types of brain tumors (medulloblastoma and glioblastoma) and between two types of Non-Hodgkins lymphoma (folicular lymphoma (FL) and diffuse large B cell lymphoma (DLBCL).

The present invention relates to classification based on the simultaneous expression monitoring of a large number (e.g., thousands) of genes using DNA microarrays or other methods developed to assess a large number of genes. Microarrays have the attractive property of allowing one to monitor multiple expression events in parallel using a single technique. Previous analytically rigorous methodologies were lacking for performing such classification in this area for many diseases or conditions, and prior methodologies have not demonstrated that reproducible gene expression patterns can be reliably found amidst the genetic noise inherent in primary biological samples. On the contrary, the present invention provides methods for class discovery and class prediction in cancer and other diseases; these methods have been particularly applied to class prediction in acute leukemias.

The present invention has several embodiments. Briefly, the embodiments generally relate to two areas: class prediction and class discovery. Class prediction refers to the assignment of particular samples to defined classes which may reflect current states or future outcomes. Class discovery refers to defining one or more previously unrecognized biological classes. In one embodiment, the invention relates to predicting or determining a classification of a sample comprising identifying a set of informative genes whose expression correlates with a class distinction among samples. This embodiment pertains to sorting genes by the degree to which their expression across all the samples correlate with the class distinction, and then determining whether the correlation is stronger than expected by chance (i.e., statistically significant). If the correlation of gene expression with class distinction is statistically significant, that gene is considered an informative or relevant gene.

Once a set of informative genes is identified, the weight given the information provided by each informative gene is determined. Each vote is a measure of how much the new sample's expression of that gene looks like the typical expression level of the gene in training samples from a particular class. The more strongly a particular gene's expression is correlated with a class distinction, the greater the weight given to the information which that gene provides. In other words, if a gene's expression is strongly correlated with a class distinction, that gene's expression will carry a great deal of weight in determining the class to which a sample belongs. Conversely, if a gene's expression is only weakly correlated with a class distinction, that gene's expression will be given little weight in determining the class to which a sample belongs to. Each informative gene to be used from the set of informative genes is assigned a weight. It is not necessary that the complete set of informative genes be used; a subset of the total informative genes can be used as desired. Using this process, a weighted voting scheme is determined, and a predictor or model for class distinction is created from a set of informative genes.

A further aspect of the invention includes assigning a biological sample to a known or putative class (i.e., class prediction) by evaluating the gene expression patterns of informative genes in the sample. For each informative gene, a vote for one or the other class is determined based on expression level. Each vote is then weighted in accordance with the weighted voting scheme described above, and the weighted votes are summed to determined the winning class for the sample. The winning class is defined as the class for which the largest vote is cast. Optionally, a prediction strength (PS) for the winning class can also be determined. Prediction strength is the margin of victory of the winning class that ranges from 0 to 1. In one embodiment, a sample can be assigned to the winning class only if the PS exceeds a certain threshold (e.g., 0.3); otherwise the assessment is considered uncertain.

Another embodiment of the invention relates to a method of discovering or ascertaining two or more classes from samples by clustering the samples based on gene expression values, to obtain putative classes (i.e., class discovery). The putative classes are validated by carrying out the class prediction steps, as described above. These embodiments are described in further detail below. In preferred embodiments, one or more steps of the methods are performed using a suitable processing means, e.g., a computer.

In one embodiment, the methods of the present invention are used to classify a sample with respect to a specific disease class or a subclass within a specific disease class. The invention is useful in classifying a sample for virtually any disease, condition or syndrome including, but not limited to, cancer, muscular dystrophy, cystic fibrosis, Cushing's Syndrome, diabetes, osteoporosis, sickle-cell anemia, autoimmune diseases (e.g., lupus, scleradoma), Chrohn's Disease, Turner's Syndrome, Down's Syndrome, Huntington's Disease, obesity, heart disease, stroke, Alzheimer's Disease, and Parkinson's Disease. That is, the invention can be used to determine whether a sample belongs to (is classified as) a specific disease category (e.g., leukemia as opposed to lymphoma) and/or to a class within a specific disease (e.g., AML as opposed to ALL).

The methods described herein correctly demonstrated the distinction between AML and ALL, as well as the distinction between B-cell and T-cell ALL. These are by far the most important distinctions known among acute leukemias, both in terms of underlying biology and clinical treatment. Finer subclassification systems have been developed for AML and ALL, but the extent to which these subclasses differ in their "fundamental properties" remains unclear. AML, for example, has been subdivided into eight types, M0–M7. However, they are all treated clinically in the same fashion, with the sole exception of M3, which comprises only 5–8% of cases. Similarly, while AML can be categorized on the basis of particular chromosome translocations, it now appears that many of the translocations target common functional pathways (e.g. the t(8;21)(q22;q22), t(9;11)(p22; q23), t(11;16)(q23;p13), t(15;17)(q21;q12) and t(11;17) (q23;q12) all appear to involve dysregulation of chromatin remodeling) (L. Z. He, et al., *Nat Genet* 18:126–35(1998); R. J. Lin, et al., *Nature* 291:811–4 (1998); S. H. Hong et al., *Proc Natl Acad Sci USA* 94:9028–33 (1998); G. David et al., *Oncogene* 16:2549–56 (1998); S. Meyers et al., *Mol Cell Biol* 13:6336–45 (1993); I. Kitabayashi et al., *EMBO J*17: 2294–3004 (1998); O. Rozenblatt-Rosen et al., *Proc Natl Acad Sci USA* 95:4152–7 (1998); B. R. Cairns et al., *Mol*

Cell Biol 16:3308–16 (1996); O. M. Sobulo et al., *Proc Natl Acad Sci USA* 94:8732–7 (1997)).

As used herein, the terms "class" and "subclass" are intended to mean a group which shares one or more characteristics. For example, a disease class can be broad (e.g., proliferative disorders), intermediate (e.g., cancer) or narrow (e.g., leukemia). The term "subclass" is intended to further define or differentiate a class. For example, in the class of leukemias, AML and ALL are examples of subclasses; however, AML and ALL can also be considered as classes in and of themselves. These terms are not intended to impart any particular limitations in terms of the number of group members. Rather, they are intended only to assist in organizing the different sets and subsets of groups as biological distinctions are made.

The invention can be used to identify classes or subclasses between samples with respect to virtually any category or response, and can be used to classify a given sample with respect to that category or response. In one embodiment the class or subclass is previously known. For example, the invention can be used to classify samples, based on gene expression patterns, as being from individuals who are more susceptible to viral (e.g., HIV, human papilloma virus, meningitis) or bacterial (e.g., chlamydial, staphylococcal, streptococcal) infection versus individuals who are less susceptible to such infections. The invention can be used to classify samples based on any phenotypic trait, including, but not limited to, obesity, diabetes, high blood pressure, intelligence, physical appearance, response to chemotherapy, and response to a particular agent. The invention can further be used to identify previously unknown biological classes.

In particular embodiments, class prediction is carried out using samples from individuals known to have the disease type or class being studied, as well as samples from individuals not having the disease or having a different type or class of the disease. This provides the ability to assess gene expression patterns across the full range of phenotypes. Using the methods described herein, a classification model is built with the gene expression levels from these samples.

In one embodiment, this model is created by identifying a set of informative or relevant genes whose expression pattern is correlated with the class distinction to be predicted. For example, the genes present in a sample are sorted by their degree of correlation with the class distinction, and this data is assessed to determine whether the observed correlations are stronger than would be expected by chance (e.g., are statistically significant). If the correlation for a particular gene is statistically significant, then the gene is considered an informative gene. If the correlation is not statistically significant, then the gene is not considered an informative gene.

The degree of correlation between gene expression and class distinction can be assessed using a number of methods. In a preferred embodiment, each gene is represented by an expression vector $v(g)+(e_1, e_2, \ldots, e_n)$, where $e_i$ denotes the expression level of gene g in $i^{th}$ sample in the initial set (S) of samples. A class distinction is represented by an idealized expression pattern $c=(c_1, c_2, \ldots, c_n)$, where $c_i=+1$ or 0 according to whether the $i^{th}$ sample belongs to class 1 or class 2. The correlation between a gene and a class distinction can be measured in a variety of ways. Suitable methods include, for example, the Pearson correlation coefficient $r(g,c)$ or the Euclidean distance $d(g^*,c^*)$ between normalized vectors (where the vectors $g^*$ and $c^*$ have been normalized to have mean 0 and standard deviation 1).

In a preferred embodiment, the correlation is assessed using a measure of correlation that emphasizes the "signal-to-noise" ratio in using the gene as a predictor. In this embodiment, $(\mu_1(g),\sigma_1(g))$ and $(\mu_2(g),\sigma_2(g))$ denote the means and standard deviations of the $\log_{10}$ of the expression levels of gene g for the samples in class 1 and class 2, respectively. $P(g,c)=(\mu_1(g)-\mu_2(g))/(\sigma_1(g)+\sigma_2(g))$, which reflects the difference between the classes relative to the standard deviation within the classes. Large values of |P(g,c)| indicate a strong correlation between the gene expression and the class distinction, while small values of |P(g,c)| indicate a weak correlation between gene expression and class distinction. The sign of P(g,c) being positive or negative corresponds to g being more highly expressed in class 1 or class 2, respectively. Note that P(g,c), unlike a standard Pearson correlation coefficient, is not confined to the range [−1,+1]. If $N_1(c,r)$ denotes the set of genes such that P(g,c) >=r, and if $N_2(c,r)$ denotes the set of genes such that P(g,c)<=r, $N_1(c,r)$ and $N_2(c,r)$ are the neighborhoods of radius r around class 1 and class 2. An unusually large number of genes within the neighborhoods indicates that many genes have expression patterns closely correlated with the class vector.

Figure 1B:
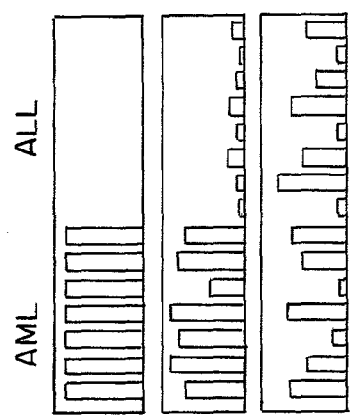
Figure 1B:
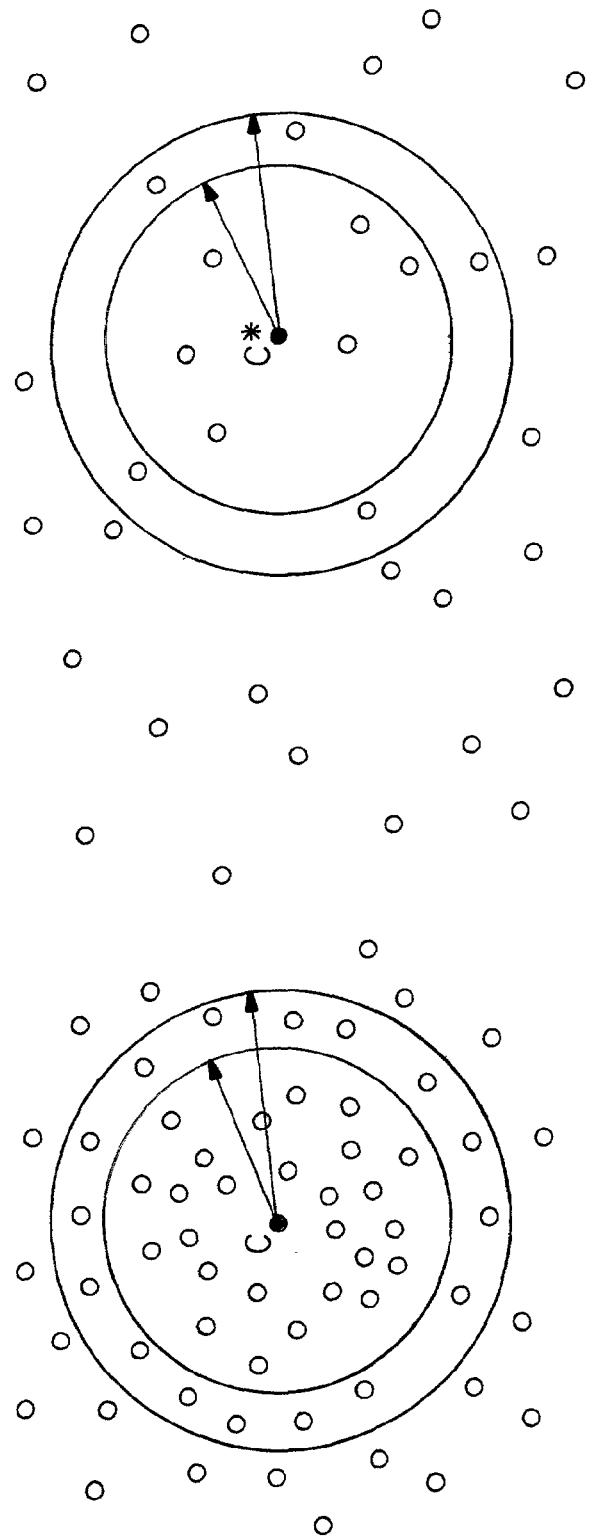

An assessment of whether the observed correlations are stronger than would be expected by chance is most preferably carried out using a "neighborhood analysis". In this method, an idealized expression pattern corresponding to a gene that is uniformly highly expressed in one class and uniformly in low levels expressed in the other class is defined, and one tests whether there is an unusually high density of genes "nearby" or "in the neighborhood of", i.e., more similar to, the idealized expression pattern than equivalent random expression patterns. The determination of whether the density of nearby genes is statistically significantly higher than expected can be carried out using known methods for determining the statistical significance of differences. One preferred method is a permutation test in which the number of genes in the neighborhood (nearby) is compared to the number of genes in similar neighborhoods around idealized expression patterns corresponding to random class distinctions, obtained by permuting the coordinates of c (FIG. 1B).

The sample assessed can be any sample that contains a gene expression product. Using the methods described herein, expression of numerous genes can be measured simultaneously. The assessment of numerous genes provides for a more accurate evaluation of the sample because there are more genes that can assist in classifying the sample.

As used herein, gene expression products are proteins, peptides, or nucleic acid molecules (e.g., mRNA, tRNA, rRNA, or cRNA) that are involved in transcription or translation. The present invention can be effectively used to analyze proteins, peptides or nucleic acid molecules that are involved in transcription or translation. The nucleic acid molecule levels measured can be derived directly from the gene or, alternatively, from a corresponding regulatory gene. All forms of gene expression products can be measured, such as spliced variants. Similarly, gene expression can be measured by assessing the level of protein or derivative thereof translated from mRNA. Sources of gene expression products are cells, lysed cells, cellular material for determining gene expression, or material containing gene expression products. Examples of such samples are blood, plasma, lymph, urine, tissue, mucus, sputum, saliva or other cell samples. Methods of obtaining such samples are known in the art.

The gene expression levels are obtained, e.g., by contacting the sample with a suitable microarray, and determining the extent of hybridization of the nucleic acid in the sample to the probes on the microarray. Once the gene expression levels of the sample are obtained, the levels are compared or evaluated against the model, and then the sample is classified. The evaluation of the sample determines whether or not the sample should be assigned to the particular disease class being studied.

The gene expression value measured or assessed is the numeric value obtained from an apparatus that can measure gene expression levels. Gene expression levels refer to the amount of expression of the gene expression product, as described herein. The values are raw values from the apparatus, or values that are optionally, rescaled, filtered and/or normalized. Such data is obtained, for example, from a gene chip probe array or Microarray (Affymetrix, Inc.)(U.S. Pat. Nos. 5,631,734, 5,874,219, 5,861,242, 5,858,659, 5,856,174, 5,843,655, 5,837,832, 5,834,758, 5,770,722, 5,770,456, 5,733,729, 5,556,752, all which are incorporated herein by reference in their entirety) and then the expression levels are calculated with software (Affymetrix GENECHIP software). The gene chip contains a variety of probe arrays that adhere to the chip in a predefined position. The chip contains thousands of probes. Nucleic acids (e.g., mRNA) from an experiment or sample which has been subjected to particular stringency conditions hybridize to the probes which exist on the chip. The nucleic acid to be analyzed (e.g., the target) is isolated, amplified and labeled with a detectable label, (e.g., $^{32}P$ or fluorescent label), prior to hybridization to the gene chip probe arrays. Once hybridization occurs, the arrays are inserted into a scanner which can detect patterns of hybridization. The hybridization data are collected as light emitted from the labeled groups which is now bound to the probe array. The probes that perfectly match the target produce a stronger signal than those that have mismatches. Since the sequence and position of each probe on the array are known, by complementarity, the identity of the target nucleic acid applied to the probe is determined. The amount of light detected by the scanner becomes raw data that the invention applies and utilizes. The gene chip probe array is only one example of obtaining the raw gene expression value. Other methods for obtaining gene expression values known in the art or developed in the future can be used with the present invention.

The data can optionally prepared by using a combination of the following: rescaling data, filtering data and normalizing data. The gene expression values can be rescaled to account for variables across experiments or conditions, or to adjust for minor differences in overall array intensity. Such variables depend on the experimental design the researcher chooses. The preparation of the data sometimes also involves filtering and/or normalizing the values prior to subjecting the gene expression values to clustering. The data, throughout its preparation and processing, may appear in table form. Partial tables appear throughout and are meant to illustrate principles and concepts of the invention. For example, Table 1 is a partial gene expression table.

TABLE 1

This is an example of a gene/sample expression table:

| gene\sample | sample 1 | sample 2 | sample 3 | sample 4 | sample 5, etc. |
|---|---|---|---|---|---|
| gene 1 | 5 | 50 | 500 | 450 | 200 |
| gene 2 | 200 | 800 | 3300 | 500 | 500 |

TABLE 1-continued

This is an example of a gene/sample expression table:

| gene\sample | sample 1 | sample 2 | sample 3 | sample 4 | sample 5, etc. |
|---|---|---|---|---|---|
| gene 3 | 30 | 31 | 29 | 30 | 31 |
| gene 4 | 5000 | 4000 | 3000 | 2000 | 1000 |
| gene 5, etc. | 10 | 30 | 50 | 70 | 90 |

Filtering the gene expression values involves eliminating any vector in which the gene expression value exhibits no change or an insignificant change. A vector is a series of gene expression values of a sample. Once the genes are filtered out then the subset of gene expression vectors that remain are referred to herein "working vectors."

Table 2 contains the working vectors from Table 1 (e.g., the gene expression values from Table 1 with those genes exhibiting an insignificant change in the gene expression being eliminated).

TABLE 2

This is an example of a gene/sample expression table:

| gene\sample | sample 1 | sample 2 | sample 3 | sample 4 | sample 5, etc. |
|---|---|---|---|---|---|
| gene 1 | 5 | 50 | 500 | 450 | 200 |
| gene 2 | 200 | 800 | 3300 | 500 | 500 |
| gene 4 | 5000 | 4000 | 3000 | 2000 | 1000 |
| gene 5, etc. | 10 | 30 | 50 | 70 | 90 |

The present invention can also involve normalizing the levels of gene expression values. The normalization of gene expression values is not always necessary and depends on the type or algorithm used to determine the correlation between a gene and a class distinction. See Example 1 for further details. The absolute level of the gene expression is not as important as the degree of correlation a gene has for a particular class. Normalization occurs using the following equation:

$$NV = \left(\frac{GEV - AGEV}{SDV}\right),$$

wherein NV is the normalized value, GEV is the gene expression value across samples, AGEV is the average gene expression value across samples, and SDV is the standard deviation of the gene expression value. Table 3, below, is the partial data table containing gene expression values which have been normalized, utilizing the values in Table 2.

TABLE 3

This is an example of a gene/sample expression table:

| Gene\Sample | Sample 1 | Sample 2 | Sample 3 | Sample 4 | Sample 5, etc. |
|---|---|---|---|---|---|
| gene 1 | −1.043 | −0.844 | 1.145 | 0.924 | −0.181 |
| gene 2 | −0.677 | −0.204 | 1.763 | −0.440 | −0.440 |
| gene 4 | 1.264 | 0.632 | 0 | −0.632 | −1.264 |
| gene 5, etc. | −1.264 | −0.632 | 0 | 0.632 | 1.264 |

Once the gene expression values are prepared, then the data is classified or is used to build the model for classification. Genes that are relevant for classification are first determined. The term "relevant genes" refers to those genes that form a correlation with a class distinction. The genes that are relevant for classification are also referred to herein as "informative genes." The correlation between gene expression and class distinction can be determined using a variety of methods; for example, a neighborhood analysis can be used. A neighborhood analysis comprises performing a permutation test, and determining probability of number of genes in the neighborhood of the class distinction, as compared to the neighborhoods of random class distinctions. The size or radius of the neighborhood is determined using a distance metric. For example, the neighborhood analysis can employ the Pearson correlation coefficient, the Euclidean distance coefficient, or a signal to noise coefficient (see Example 1). The relevant genes are determined by employing, for example, a neighborhood analysis which defines an idealized expression pattern corresponding to a gene that is uniformly high in one class and uniformly low in other class(es). A disparity in gene expression exists when comparing the level of expression in one class with other classes. Such genes are good indicators for evaluating and classifying a sample based on its gene expression. In one embodiment, the neighborhood analysis utilizes the following signal to noise routine:

$$P(g,c)=(\mu_1(g)-\mu_2(g))/(\sigma_1(g)+\sigma_2(g)),$$

wherein g is the gene expression value; c is the class distinction, $\mu_1(g)$ is the mean of the expression levels for g for a first class; $\mu_2(g)$ is the mean of the expression levels for g for a second class; $\sigma_1(g)$ is the standard deviation for g the first class; and $\sigma_2(g)$ is the standard deviation for the second class. The invention includes classifying a sample into one of two classes, or into one of multiple (a plurality of) classes.

Particularly relevant genes are those genes that are best suited for classifying samples. The step of determining the relevant genes also provides the genes that play a role in the phenotype of the class being tested or evaluated. For example, as described herein, samples are classified into various types or classes of cancer, in particular, leukemia disease classes. In determining which genes are best suited for classifying a sample to be tested, this step also determines the genes that are important in the pathogenesis of leukemia disease classes. One or more of these genes provides target(s) for drug therapy for the disease class. Hence, the present invention embodies methods for determining the relevant genes for classification of samples as well as methods for determining the importance of a gene involved in the disease class as to which samples are being classified. Consequently, the methods of the present invention also pertain to determining drug target(s) based on genes that are involved with the disease being studied, and the drug, itself, as determined by this method.

The next step for classifying genes involves building or constructing a model or predictor that can be used to classify samples to be tested. One builds the model using samples for which the classification has already been ascertained, referred to herein as an "initial dataset." Once the model is built, then a sample to be tested is evaluated against the model (e.g., classified as a function of relative gene expression of the sample with respect to that of the model).

A portion of the relevant genes, determined as described above, can be chosen to build the model. Not all of the genes need to be used. The number of relevant genes to be used for building the model can be determined by one of skill in the art. For example, out of 1000 genes that demonstrate a high correlation to a class distinction, 25, 50, 75 or 100 or more of these gene can be used to build the model.

The model or predictor is built using a "weighted voting scheme" or "weighted voting routine." A weighted voting scheme allows these informative genes to cast weighted votes for one of the classes. The magnitude of the vote is dependant on both the expression level and the degree of correlation of the gene expression with the class distinction. The larger the disparity or difference between gene expression of a gene from one class and the next, the larger the vote the gene will cast. A gene with a larger difference is a better indicator for class distinction, and so casts a larger vote.

The model is built according to the following weighted voting routine:

$$V_g = a_g(x_g - b_g),$$

wherein $V_g$ is the weighted vote of the gene, g; $a_g$ is the correlation between gene expression values and class distinction, P(g,c), as defined herein; $b_g=[\mu_1(g)+\mu_2(g)]/2$ which is the average of the mean $\log_{10}$ expression value in a first class and a second class; $x_g$ is the $\log_{10}$ gene expression value in the sample to be tested. A positive weighted vote is a vote for the new sample's membership in the first class, and a negative weighted vote is a vote for the new sample's membership in the second class. The total vote $V_1$ for the first class is obtained by summing the absolute values of the positive votes over the informative genes, while the total vote $V_2$ for the second class is obtained by summing the absolute values of the negative votes.

A prediction strength can also be measured to determine the degree of confidence the model classifies a sample to be tested. The prediction strength conveys the degree of confidence of the classification of the sample and evaluates when a sample cannot be classified. There may be instances in which a sample is tested, but does not belong to a particular class. This is done by utilizing a threshold wherein a sample which scores below the determined threshold is not a sample that can be classified (e.g., a "no call"). For example, if a model is built to determine whether a sample belongs to one of two leukemia classes, but the sample is taken from an individual who does not have leukemia, then the sample will be a "no call" and will not be able to be classified (see Example 1 for details on how to calculate the prediction strength). The prediction strength threshold can be determined by the skilled artisan based on known factors, including, but not limited to the value of a false positive classification versus a "no call".

Once the model is built, the validity of the model can be tested using methods known in the art. One way to test the validity of the model is by cross-validation of the dataset. To perform cross-validation, one of the samples is eliminated and the model is built, as described above, without the eliminated sample, forming a "cross-validation model." The eliminated sample is then classified according to the model, as described herein. This process is done with all the samples of the initial dataset and an error rate is determined. The accuracy the model is then assessed. This model should classify samples to be tested with high accuracy for classes that are known, or classes have been previously ascertained or established through class discovery, as described in detail below and in Example 2. Another way to validate the model is to apply the model to an independent data set, as described in more detail herein. Other standard biological or medical research techniques, known or developed in the future, can be used to validate class discovery or class prediction.

An aspect of the invention also includes ascertaining or discovering classes that were not previously known, or validating previously hypothesized classes. This process is referred to herein as "class discovery." This embodiment of the invention involves determining the class or classes not previously known, and then validating the class determination (e.g., verifying that the class determination is accurate).

To ascertain classes that were not previously known or recognized, or to validate classes which have been proposed on the basis of other findings, the samples are grouped or clustered based on gene expression levels. The gene expression levels of a sample from a gene expression pattern and the samples having similar gene expression patterns are grouped or clustered together. The group or cluster of samples identifies a class. This clustering methodology can be applied to identify any classes in which the classes differ based on genetic expression.

Determining classes that were not previously known is performed by the present methods using a clustering routine. The present invention can utilize several clustering routines to ascertain previously unknown classes, such as Bayesian clustering, k-means clustering, hierarchical clustering, and Self Organizing Map (SOM) clustering (see, for example, U.S. Provisional Application No. 60/124,453, entitled, "Methods and Apparatus for Analyzing Gene Expression Data," by Tayamo, et al., filed Mar. 15, 1999, and U.S. patent application Ser. No. 09/525,142, entitled, "Methods and Apparatus for Analyzing Gene Expression Data," by Tayamo, et al., filed Mar. 14, 2000, the teachings of which are incorporated herein by reference in their entirety).

Once the gene expression values are prepared, then the data is clustered or grouped. One particular aspect of the invention utilizes SOMs, a competitive learning routine, for clustering gene expression patterns to ascertain the classes. SOMs impose structure on the data, with neighboring nodes tending to define 'related' clusters or classes.

SOMs are constructed by first choosing a geometry of 'nodes'. Preferably, a 2 dimensional grid (e.g., a 3×2 grid) is used, but other geometries can be used. The nodes are mapped into k-dimensional space, initially at random and then interactively adjusted. Each iteration involves randomly selecting a vector and moving the nodes in the direction of that vector. The closest node is moved the most, while other nodes are moved by smaller amounts depending on their distance from the closest node in the initial geometry. In this fashion, neighboring points in the initial geometry tend to be mapped to nearby points in k-dimensional space. The process continues for several (e.g., 20,000–50,000) iterations.

The number of nodes in the SOM can vary according to the data. For example, the user can increase the number of Nodes to obtain more clusters. The proper number of clusters allows for a better and more distinct representation of the particular cluster of cluster of samples. The grid size corresponds to the number of nodes. For example a 3×2 grid contains 6 nodes and a 4×5 grid contains 20 nodes. As the SOM algorithm is applied to the samples based on gene expression data, the nodes move toward the sample cluster over several iterations. The number of Nodes directly relates to the number of clusters. Therefore, an increase in the number of Nodes results in an increase in the number of clusters. Having too few nodes tends to produce patterns that are not distinct. Additional clusters result in distinct, tight clusters of expression. The addition of even more clusters beyond this point does not result any fundamentally new patterns. For example, one can choose a 3×2 grid, a 4×5 grid, and/or a 6×7 grid, and study the output to determine the most suitable grid size.

A variety of SOM algorithms exist that can cluster samples according to gene expression vectors. The invention utilizes any SOM routine (e.g., a competitive learning routine that clusters the expression patterns), and preferably, uses the following SOM routine:

$$f_{i+1}(N)=f_i(N)+\tau(d(N,N_P), i)(P-f_i(N)),$$

wherein i=number of iterations, N=the node of the self organizing map, $\tau$=learning rate, P=the subject working vector, d=distance, $N_p$=node that is mapped nearest to P, and $f_i(N)$ is the position of N at i.

Once the samples are grouped into classes using a clustering routine, the putative classes are validated. The steps for classifying samples (e.g., class prediction) can be used to verify the classes. A model based on a weighted voting scheme, as described herein, is built using the gene expression data from the same samples for which the class discovery was performed. Such a model will perform well (e.g., via cross validation and via classifying independent samples) when the classes have been properly determined or ascertained. If the newly discovered classes have not been properly determined, then the model will not perform well (e.g., not better than predicting by the majority class). All pairs of classes discovered by the chosen class discovery method were compared. For each pair $C_1$, $C_2$, S is the set of samples in either $C_1$ or $C_2$. Class membership (either $C_1$ or $C_2$) was predicted for each sample in S by the cross validation method described herein. The median PS (over the |S| predictions) to be a measure of how predictable the class distinction is from the given data. A low median PS value (e.g., near 0.3) indicates either spurious class distinction or an insufficient amount of data to support a real distinction. A high median PS value (e.g., 0.8) indicates a strong, predictable class distinction.

The class discovery techniques above can be used to identify the fundamental subtypes of any disorder, e.g., cancer. As described herein, the methods have been successfully applied to lymphomas. In particular, class discovery methods have been applied to the following: large B-cell and follicular lymphoma; brain glioma and medulloblastoma; and T-Cell and B-cell ALL. See FIGS. 7–12. In general, such studies may benefit from careful experimental design to avoid potential experimental artifacts, especially in the case of solid tumors. Biopsy specimens, for example, might have gross differences in the proportion of surrounding stromal cells. Blind application of class discovery could result in identifying classes reflecting the proportion of stromal contamination in the samples, rather than underlying tumor biology. Such 'classes' would be real and reproducible, but would not be of biological or clinical interest. Various approaches could be used to avoid such artifacts, such as microscopic examination of tumor samples to ensure comparability, purification of tumor cells by flow sorting or laser-capture microdissection, computational analysis that excludes genes expressed in stromal cells, and confirmation of candidate marker genes by RNA in situ hybridization or immunohistochemistry to tumor sections.

Class discovery methods could also be used to search for fundamental mechanisms that cut across distinct types of cancers. For example, one might combine different cancers (for example, breast tumors and prostate tumors) into a single dataset, eliminate those genes that correlate strongly with tissue type, and then cluster the samples based on the remaining genes. Moreover, the class predictor described here could be adapted to a clinical setting (with an appropriate custom array containing the 50 genes to be monitored and a standardized procedure for sample handling). Such a test would most likely supplement rather than replace existing leukemia diagnostics. Indeed, this would provide an opportunity to gain clinical experience with the use of expression-based class predictors in a well-studied cancer, before applying them to cancers with less well-developed diagnostics.

Classification of the sample gives a healthcare provider information about a classification to which the sample belongs, based on the analysis or evaluation of multiple genes. The methods provide a more accurate assessment that traditional tests because multiple genes or markers are analyzed, as opposed to analyzing one or two markers as is done for traditional tests. The information provided by the present invention, alone or in conjunction with other test results, aids the healthcare provider in diagnosing the individual.

Also, the present invention provides methods for determining a treatment plan. Once the health care provider knows to which disease class the sample, and therefore, the individual belongs, the health care provider can determine an adequate treatment plan for the individual. Different disease classes often require differing treatments. As described herein, individuals having a particular type or class of cancer can benefit from a different course of treatment, than an individual having a different type or class of cancer. Properly diagnosing and understanding the class of disease of an individual allows for a better, more successful treatment and prognosis.

In addition to classifying or ascertaining classes for disease types, the present invention can be used for other purposes. For example, the present invention can be used to ascertain classes for or classify a sample from an individual into a classification for persons who are expected to live a long life (e.g., live over 90 or 100 years). To determine whether an individual has the genes for longevity, a model, using the methods described herein (e.g., a weighted voting scheme), can be built using the genetic information from individuals who have had a long life, e.g., over 80 years, 90 years, or 100 years, etc., and individuals who do not live a long life, e.g., less than 60 years, or 50 years. Once a model is built, a sample from an individual is evaluated against the model. Classification of the sample to be tested can be made indicating whether the individual has the genes that are important or relevant in living a long or not so long life. The detailed steps of performing the classification are described herein.

Other applications of the invention include ascertaining classes for or classifying persons who are likely to have successful treatment with a particular drug or regiment. Those interested in determining the efficacy of a drug can utilize the methods of the present invention. During a study of the drug or treatment being tested, individuals who have a disease may respond well to the drug or treatment, and others may not. Often, disparity in treatment efficacy may be the result of genetic variations among the individuals. Samples are obtained from individuals who have been subjected to the drug being tested and who have a predetermined response to the treatment. A model can be built from a portion of the relevant genes from these samples, using the weighted voting scheme described herein. A sample to be tested can then be evaluated against the model and classified on the basis of whether treatment would be successful or unsuccessful. The company testing the drug could provide more accurate information regarding the class of individuals for which the drug is most useful. This information also aids a healthcare provider in determining the best treatment plan for the individual.

Another application of the present invention is classification of a sample from an individual to determine whether he or she is more likely to contract a particular disease or condition. For example, persons who are more likely to contract heart disease or high blood pressure can have genetic differences from those who are less likely to suffer from these diseases. A model, using the methods described herein, can be built from individuals who have heart disease or high blood pressure, and those who do not using a weighted voting scheme. Once the model is built, a sample from an individual can be tested and evaluated with respect to the model to determine to which class the sample belongs. An individual who belongs to the class of individuals who have the disease, can take preventive measures (e.g., exercise, aspirin, etc.). Heart disease and high blood pressure are examples of diseases that can be classified, but the present invention can be used to classify samples for virtually any disease.

More generally, class predictors may be useful in a variety of settings. First, class predictors can be constructed for known pathological categories, reflecting a tumor's cell of origin, stage or grade. Such predictors could provide diagnostic confirmation or clarify unusual cases. Second, the technique of class prediction can be applied to distinctions relating to future clinical outcome, such as drug response or survival.

In summary, understanding heterogeneity among tumors will be important for cancer diagnosis, prognosis and treatment. A timely example is the recognition that a subset of breast tumors express the HER2 receptor tyrosine kinase, leading to the development of an antibody strategy effective in treating this subset of patients (J. Baselga et al., *J. Clin Oncol* 14:737–44 (1996); M. D. Pegram et al., *J. Clin Oncol* 16:2659–71 (1998)). The future success of cancer treatment will surely require more systematic molecular genetic classification of tumors, allowing better ways to match patients with therapies. The combination of comprehensive knowledge of the human genome, technologies for expression monitoring, and analytical methods for classification encompassed by the present invention provide the tools needed to take on this challenge.

After the samples are classified, the output (e.g., output assembly) is provided (e.g., to a printer, display or to another software package such as graphic software for display). The output assembly can be a graphical representation. The graphical representation can be color coordinated with shades of contiguous colors (e.g., blue, red, etc.). One can then analyze or evaluate the significance of the sample classification. The evaluation depends on the purpose for the classification or the experimental design. For example, if one were determining whether the sample belongs to a particular disease class, then a diagnosis or a course of treatment can be determined.

Figure 6:
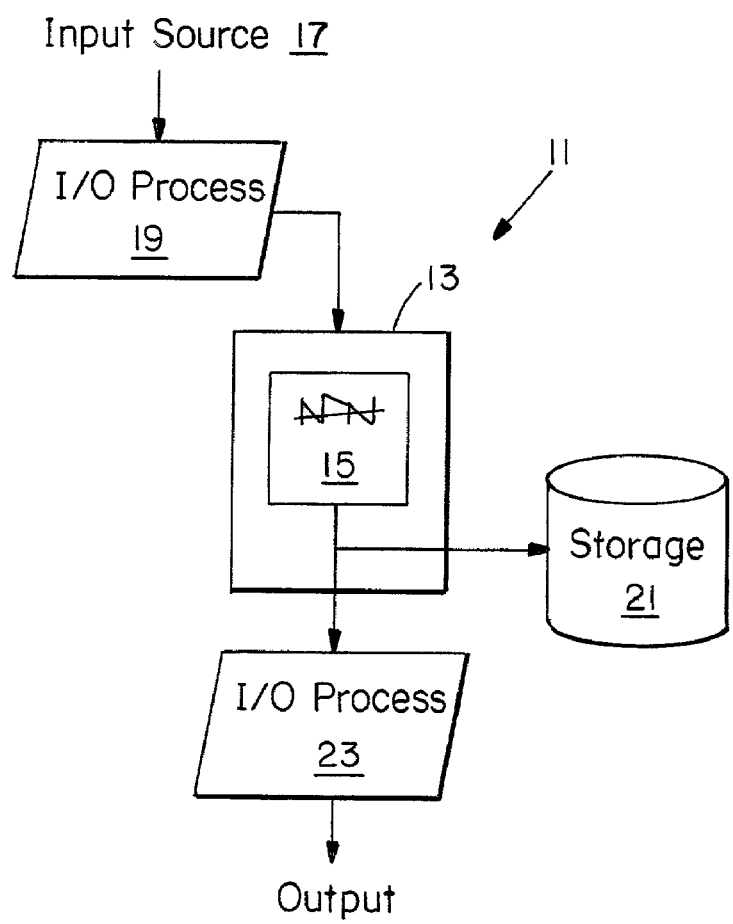
FIG. 6 is a block diagram of a network employing the methods of the present invention.
Figure 7:
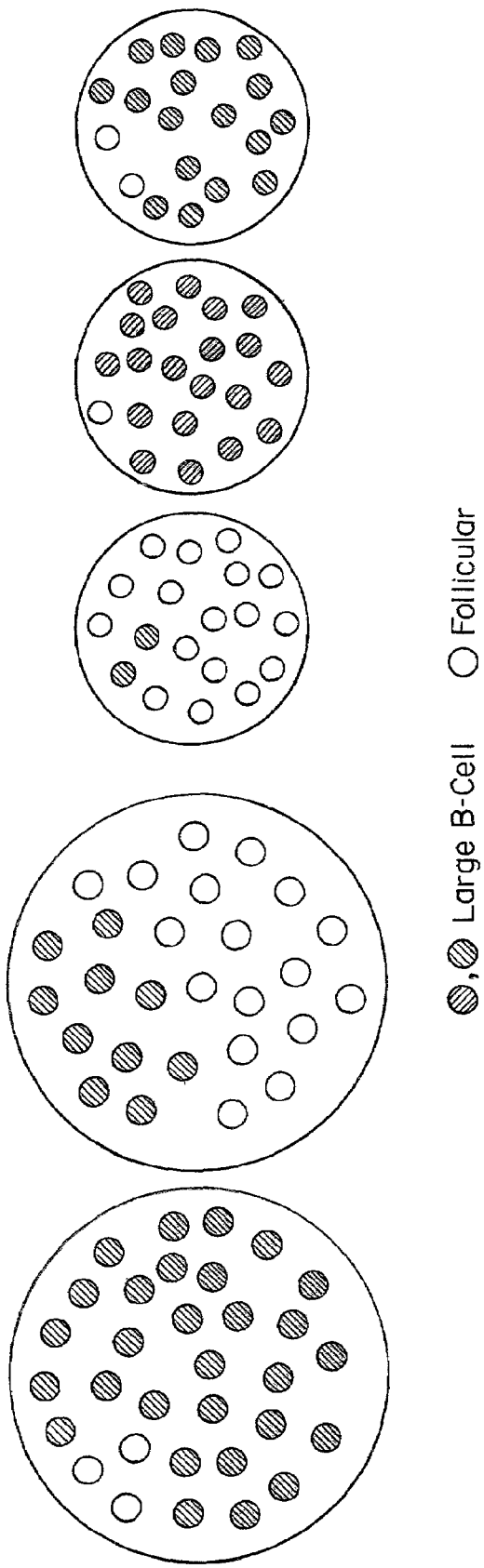
FIG. 7 is a graphical representation showing an example of SOM class discovery with respect to Large B-cell Lymphoma and Follicular Lymphoma.
Figure 8:
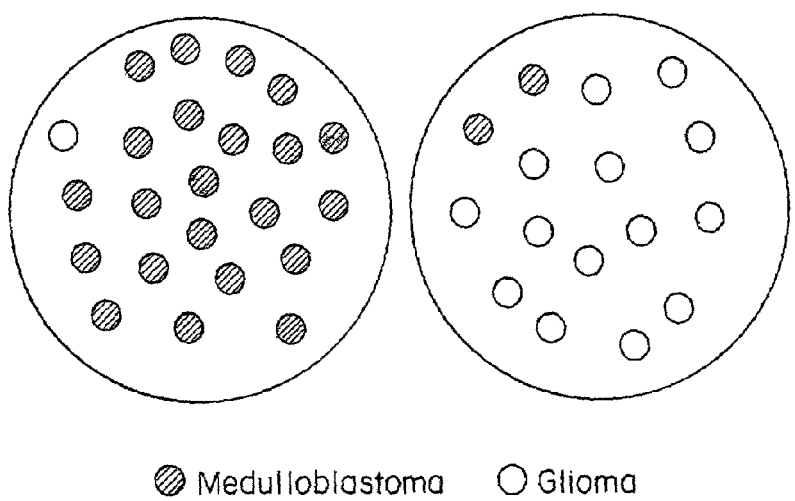
FIG. 8 is a graphical representation showing an example of SOM class discovery with respect to Brain Glioma and Medulloblastoma.
Figure 9:
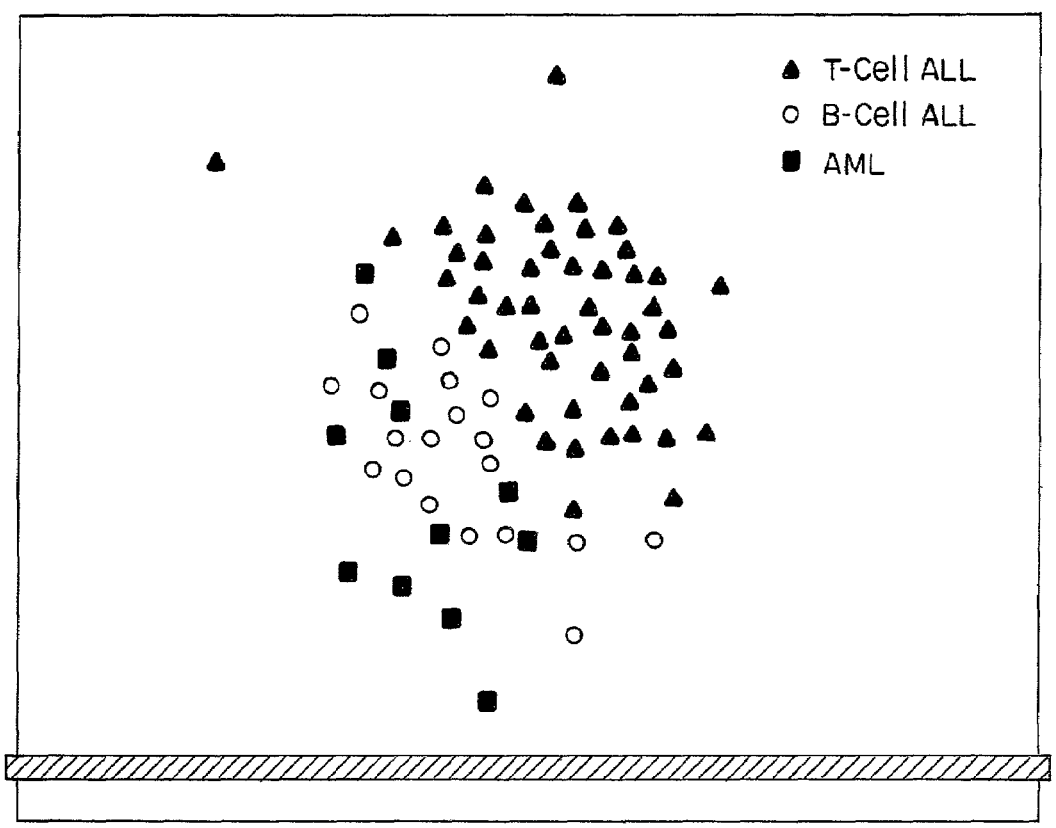
FIG. 9 is a schematic showing the multidimensional scaling of leukemia samples.
Figure 11A:
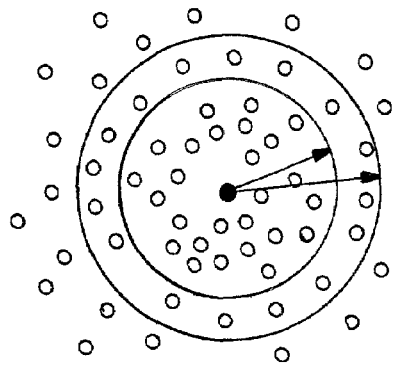
FIGS. 11A–D are illustration showing the assessment of statistical significance of gene-class correlations using neighborhood analysis.
Figure 11B:
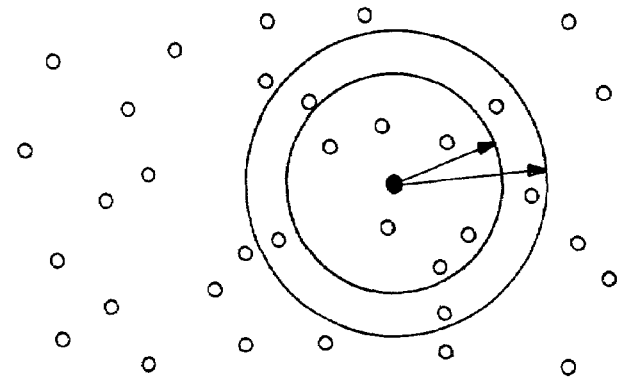
Figure 11C:
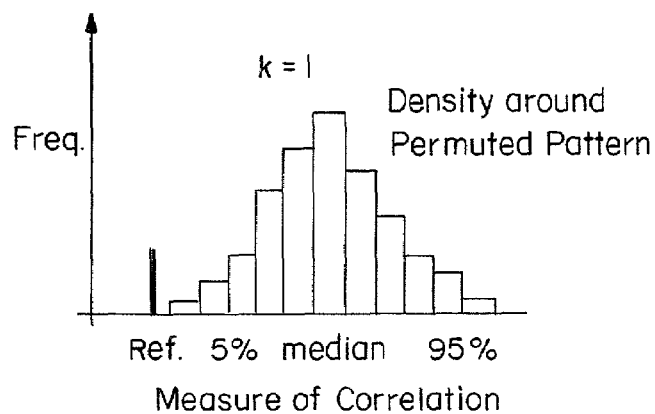
Figure 11D:
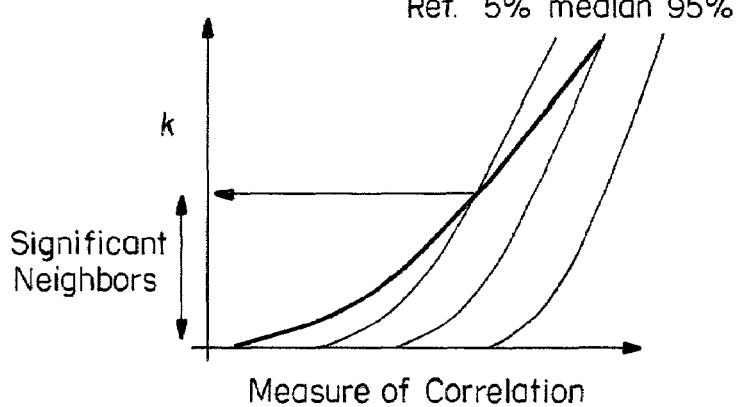

Referring to FIG. 6, a computer system embodying a software program 15 (e.g., a processor routine) of the present invention is generally shown at 11. The computer system 11 employs a host processor 13 in which the operation of software programs 15 are executed. An input device or source such as on-line data from a work-station terminal, a sensor system, stored data from memory and the like provides input to the computer system 11 at 17. The input is pre-processed by I/O processing 19 which queues and/or formats the input data as needed. The pre-processed input data is then transmitted to host processor 13 which processes the data through software 15. In particular, software 15 maps the input data to an output pattern and generates classes indicated on output for either memory storage 21 or display through an I/O device, e.g., a work-station display monitor, a printer, and the like. I/O processing (e.g., formatting) of the content is provided at 23 using techniques common in the art.

Receiving the gene expression data refers to delivering data, which may or may not be pre-processed (e.g., rescaled, filtered, and/or normalized), to the software 15 (e.g., processing routine) that classifies the samples. A processor routine refers to a set of commands that carry out a specified function. The invention utilizes a processor routine in which the weighted voting algorithm or a clustering algorithm classifies or ascertains classes for samples based on gene expression levels. Once the software 15 classifies the vectors or ascertains the previously unknown classes, then an output is provided which indicates the same. Providing an output refers to providing this information to an output (I/O) device.

The invention will be further described with reference to the following non-limiting examples. The teachings of all the patents, patent applications and all other publications and websites cited herein are incorporated by reference in their entirety.

Exemplification

EXAMPLE 1

Class Prediction

The work described herein began with the question of class prediction or how one could use an initial collection of samples belonging to known classes (such as AML and ALL) to create a 'class predictor' to classify new, unknown samples. An analytical method (FIG. 1A) was developed and first tested on distinctions that are easily made at the morphological level, such as distinguishing normal kidney from renal cell carcinoma. Six normal kidney biopsies and six kidney tumors (renal cell carcinomas, RCC) were compared using the methods outlined below for the leukemias. Neighborhood analysis showed a high density of genes correlated with the distinction. Class predictors were constructed using 50 genes, and the predictions proved to be 100% accurate in cross-validation. The informative genes more highly expressed in normal kidney compared to RCC included 13 metabolic enzymes, two ion channels, and three isoforms of the heavy metal chelator metallothionein, all of which are known to function in normal kidney physiology. Those more highly expressed in RCC than normal kidney included interleukin-1, an inflammatory cytokine known to be responsible for the febrile response experienced by patients with RCC, and CCND1, a D-type cyclin known to be amplified in some cases of RCC.

The initial leukemia dataset consisted of 38 bone marrow samples (27 ALL, 11 AML) obtained from acute leukemia patients at the time of diagnosis. The initial 38 samples were all derived from bone marrow aspirates performed at the time of diagnosis, prior to any chemotherapy. After informed consent was obtained, mononuclear cells were collected by Ficoll sedimentation and total RNA extracted using either Trizol (Gibco/BRL) or RNAqueous reagents (Ambion) according to the manufacturers' directions. The 27 ALL samples were derived from childhood ALL patients treated on Dana-Farber Cancer Institute (DFCI) protocols between the years of 1980 and 1999. Samples were randomly selected from the leukemia cell bank based on availability. The 11 adult AML samples were similarly obtained from the Cancer and Leukemia Group B (CALGB) leukemia cell bank. Samples were selected without regard to immunophenotype, cytogenetics, or other molecular features.

The independent samples used to confirm the results included a broader range of samples, including peripheral blood samples and childhood AML cases. The independent set of leukemia samples was comprised of 24 bone marrow and 10 peripheral blood specimens, all obtained at the time of leukemia diagnosis. The ALL samples were obtained from the DFCI childhood ALL bank (n=17) or Stt. Jude Children's Research Hospital (SJCRH) (n=3). Whereas the AML samples in the initial data set were all derived from adult patients, the AML samples in the independent data set were derived from both adults and children. The samples were obtained from either the CALGB (adults AML, n=4), SJCRH (childhood AML, n=5), or the Children's Cancer Group (childhood AML, n=5) leukemia banks. The samples were processed as described earlier, with the exception of the samples from SJCRH which employed a different protocol. The SJCRH samples were subjected to hypotonic lysis (rather than Ficoll sedimentation) and RNA was extracted using an aqueous extraction method (Qiagen).

RNA prepared from bone marrow mononuclear cells was hybridized to high-density oligonucleotide microarrays, produced by Affymetrix and containing probes for 6817 human genes. A total of 3–10 µg of total RNA from each sample was used to prepare biotinylated target essentially as previously described, with minor modifications (see P. Tamayo et al., *Proc Natl Acad Sci USA* 96:2907–2912 (1999); L. Wodicka et al., *Nature Biotechnology* 15:1359–67 (1997)). Total RNA was used to create double-stranded cDNA using an oligo-dT primer containing a T7 RNA polymerase binding site. This cDNA was then used as a template for T7-mediated in vitro transcription in the presence of biotinylated UTP and CTP (Enzo Diagnostics). This process generally results in 50–100 fold linear amplification of the starting RNA. 15 µg of biotinylated RNA was fragmented in $MgCl_2$ at 95° C. to reduce RNA secondary structure. The RNA was hybridized overnight to Affymetrix high density oligonucleotide microarrays containing probes for 5920 known human genes and 897 expressed sequence tags (ESTs). Following washing steps, the arrays were incubated with streptavidin-phycoerythrin (Molecular Probes) and a biotinylated anti-streptavidin antibody (Vector Laboratories), which results in approximately 5-fold signal amplification. The arrays were scanned with an Affymetrix scanner, and the expression levels for each gene calculated using Affymetrix GENE-CHIP software. In addition to calculating an expression level for each gene, GENECHIP also generates a confidence measure relating to the likelihood that each gene is actually expressed. High confidence calls receive a Present ('P') call, whereas less confident measurements are called Absent ('A'). The arrays were then resealed in order to adjust for minor differences in overall array intensity. These scaling factors were obtained by selecting a reference sample, and generating a scattergram comparing the reference expression levels to the expression levels for each of the other samples in the data set. Only genes receiving 'P' calls in both the reference and test sample were used in this part of the analysis. A linear regression model was used to calculate the scaling factor (slope) for each sample, and the raw expression values were adjusted accordingly. Subsequent data analysis included all expression measurements, regardless of their confidence calls. Reproducibility experiments comparing repeated hybridizations of a single sample to microarrays indicated that expression levels were reproducible within 2-fold within the range of 100–16,000 expression units. An expression level of 100 units was assigned to all genes whose measured expression level was <100, because expression measurements were poorly reproducible below this level. Similarly, a ceiling of 16,000 was used because fluorescence saturated above this level.

Samples were subjected to a priori quality control standards regarding the amount of labeled RNA available for each sample and the quality of the scanned microarray images. Samples yielding less than 15 µg of biotinylated RNA were excluded from the study. In addition, samples were excluded if they met any of the following three pre-determined criteria for quality control failure: too few genes were defined as 'Present' by the GENECHIP software (typical samples gave 'Present' calls for an average of 1904 of the 6817 genes surveyed; samples which were excluded gave 'Present' calls for fewer than 1000 genes); the scaling factor required to scale the expression data was too large (>3-fold); or the microarray contained visible artifacts (such as scratches). The methods described herein are thus not entirely automated, since the third criterion involves visual inspection of the scanned array data. A total of 80 samples were subjected to microarray hybridization. Of these, 8 (10%) failed the a priori quality control criteria and were therefore excluded. There were four failures due to too few 'Present' calls, two failures due to too large a scaling factor, and two failures due to microarray defects. All 6,817 genes on the microarray were analyzed for each sample.

The first issue was to explore whether there were genes whose expression pattern was strongly correlated with the class distinction to be predicted. The 6817 genes were sorted by their degree of correlation with the AML/ALL class distinction. Each gene is represented by an expression vector $v(g)=(e_1, e_2, \ldots, e_n)$, where $e_i$ denotes the expression level of gene g in $i^{th}$ sample in the initial set S of samples. A class distinction is represented by an idealized expression pattern $c=(c_1, c_2, \ldots, c_n)$, where $c_i=+1$ or 0 according to whether the $i^{th}$ sample belongs to class 1 or class 2. One can measure correlation between a gene and a class distinction in a variety of ways. One can use the Pearson correlation coefficient $r(g,c)$ or the Euclidean distance $d(g^*,c^*)$ between normalized vectors (where the vectors $g^*$ and $c^*$ have been normalized to have mean 0 and standard deviation 1).

In these experiments, a measure of correlation was employed that emphasizes the 'signal-to-noise' ratio in using the gene as a predictor. Let $(\mu_1(g),\sigma_1(g))$ and $(\mu_2(g),\sigma_2(g))$ denote the means and standard deviations of the $\log_{10}$ of the expression levels of gene g for the samples in class 1 and class 2, respectively. Let $P(g,c)=(\mu_1(g)-\mu_2(g))/(\sigma_1(g)+\sigma_2(g))$, which reflects the difference between the classes relative to the standard deviation within the classes. Large values of $|P(g,c)|$ indicate a strong correlation between the gene expression and the class distinction, while the sign of $P(g,c)$ being positive or negative corresponds to g being more highly expressed in class 1 or class 2. Note that $P(g,c)$, unlike a standard Pearson correlation coefficient, is not confined to the range $[-1, +1]$. Let $N_1(c,r)$ denote the set of genes such that $P(g,c)>=r$, and let $N_2(c,r)$ denote the set of genes such that $P(g,c)<=-r$. $N_1(c,r)$ and $N_2(c,r)$ are referred to as the neighborhoods of radius r around class 1 and class 2. An unusually large number of genes within the neighborhoods indicates that many genes have expression patterns closely correlated with the class vector.

The challenge was to know whether the observed correlations were stronger than would be expected by chance. This was addressed by developing a method called 'neighborhood analysis' (FIG. 1B). FIG. 1B shows that class distinction is represented by an idealized expression pattern c, in which the expression level is uniformly high in class 1 and uniformly low in class 2. Each gene is represented by an expression vector, consisting of its expression level in each of the tumor samples. In the figure, the dataset consists of 12 samples comprised of 6 AMLs and 6 ALLs. Gene $g_1$ is well correlated with the class distinction, while $g_2$ is poorly correlated. Neighborhood analysis involves counting the number of genes having various levels of correlation with c. The results are compared to the corresponding distribution obtained for random idealized expression patterns $c^*$, obtained by randomly permuting the coordinates of c. An unusually high density of genes indicates that there are many more genes correlated with the pattern than expected by chance. One defines an 'idealized expression pattern' corresponding to a gene that is uniformly high in one class and uniformly low in the other class. One tests whether there is an unusually high density of genes 'nearby' (that is, similar to) this idealized pattern, as compared to equivalent random patterns.

Figure 2A:
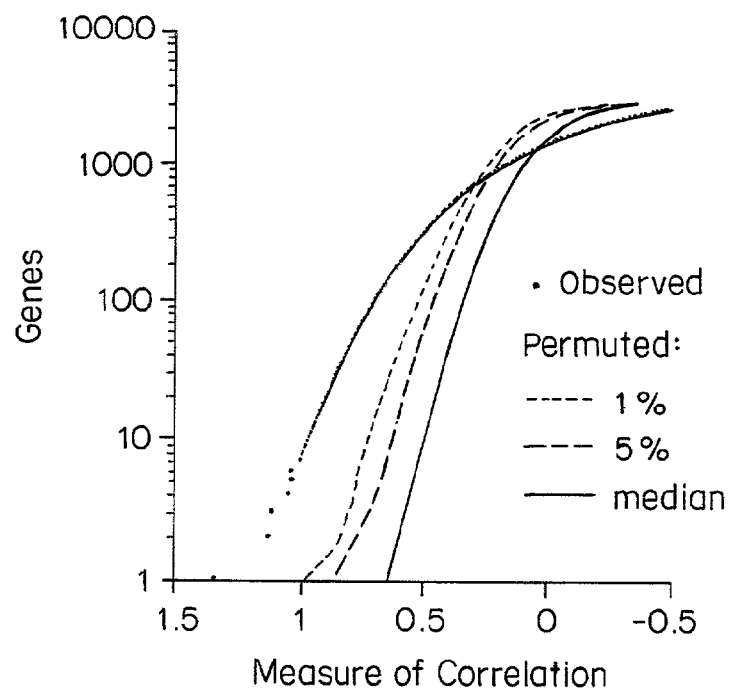
FIGS. 2A–B are scatterplots showing a neighborhood analysis of genes correlating to Acute Lymphoblastic Leukemia (ALL.
Figure 2B:
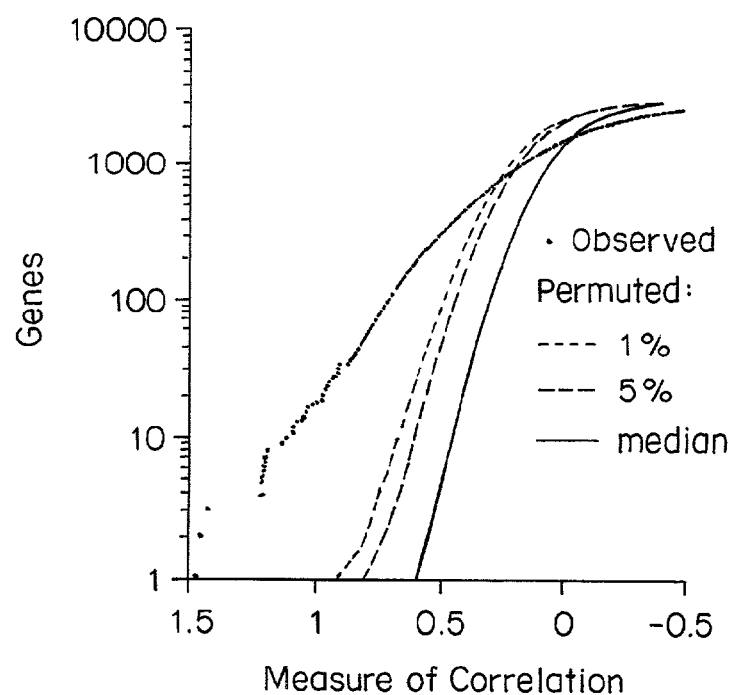

The 38 acute leukemia samples were subjected to neighborhood analysis and revealed a strikingly high density of genes correlated with the AML-ALL distinction. Roughly 1100 genes were more highly correlated with the AML-ALL class distinction than would be expected by chance (FIGS. 2A–B). FIGS. 2A–B shows the number of genes within various 'neighborhoods' of the ALL/AML class distinction together with curves showing the 5% and 1% significance levels for the number of genes within corresponding neighborhoods of the randomly permuted class distinctions. Genes more highly expressed in ALL compared to AML are shown in the left panel; those more highly expressed in AML compared to ALL are shown in right panel. Note the large number of genes highly correlated with the class distinction. In the left panel (higher in ALL), the number of genes with correlation $P(g,c)>0.30$ was 709 for the AML-ALL distinction, but had a median of 173 genes for random class distinctions. Note that $P(g,c)=0.30$ is the point where the observed data intersects the 1% significance level, meaning that 1% of random neighborhoods contain as many points as the observed neighborhood round the AML-ALL distinction. Similarly, in the right panel (higher in AML), 711 genes with $P(g,c)>0.28$ were observed, whereas a median of 136 genes is expected for random class distinctions.

A permutation test was used to calculate whether the density of genes in a neighborhood was statistically significantly higher than expected. The number of genes in the neighborhood were compared to the number of genes in similar neighborhoods around idealized expression patterns corresponding to random class distinctions, obtained by permuting the coordinates of c. 400 permutations were performed, and the 5% and 1% significance levels were determined for the number of genes contained within neighborhoods of various levels of correlation with c. On the basis of these data, the creation of a gene-based predictor was attempted.

Figure 1C:
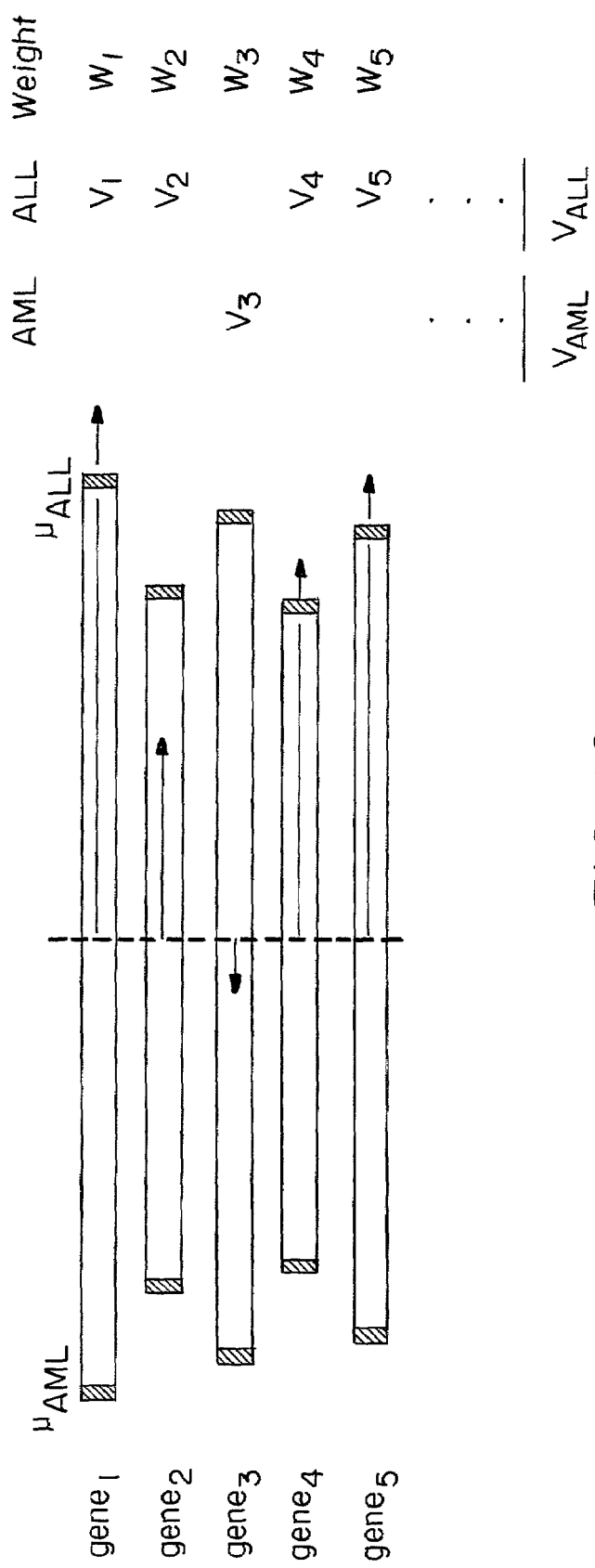

The second issue was how to create a 'class predictor' capable of assigning a new sample to one of two classes. A procedure was developed in which 'informative genes' each cast 'weighted votes' for one of the classes, with the magnitude of each vote dependent on both the expression level in the new sample and on the degree of that gene's correlation with the class distinction (FIG. 1C). The prediction of a new sample is based on 'weighted votes' of a set of informative genes. Each such gene $g_1$ votes for either AML or ALL, depending on whether its expression level $x_1$ in the sample is closer to $\mu_{AML}$ or $\mu_{ALL}$ (which denote, respectively, the mean expression levels of AML and ALL in a set of reference samples). The magnitude of the vote is $w_i v_i$, where $w_i$ is a weighting factor that reflects how well the gene is correlated with the class distinction and $v_i=|x_i-(\mu_{AML}+\mu_{ALL})/2|$ reflects the deviation of the expression level in the sample from the average of $\mu_{AML}$ and $\mu_{ALL}$. The votes for each class are summed to obtain total votes $V_{AML}$ and $V_{ALL}$. The sample is assigned to the class with the higher vote total, provided that the prediction strength exceeds a predetermined threshold. The prediction strength reflects the margin of victory and is defined as $(V_{win}-V_{lose})/(V_{win}+V_{lose})$, where as $V_{win}$ and $V_{lose}$ are the respective vote totals for the winning and losing classes.

The set of informative genes consists of the n/2 genes closest to a class vector high in class 1 (i.e., P(g,c) as large as possible) and the n/2 genes closest to class 2 (i.e., −P(g,c) as large as possible). The number n of informative genes is the only free parameter in defining the class predictor. For the AML-ALL distinction, n was chosed somewhat arbitrarily to be 50, but the results were quite insensitive to this choice.

The class predictor is uniquely defined by the initial set S of samples and the set of informative genes. Parameters ($a_g$, $b_g$) are defined for each informative gene. The value $a_g=P(g,c)$ reflects the correlation between the expression levels of g and the class distinction. The value $b_g=(\mu_1(g)+\mu_2(g))/2$ is the average of the mean $\log_{10}$ expression values in the two classes. Consider a new sample X to be predicted. Let $x_g$ denote the normalized $\log_{10}$ (expression level) of gene g in the sample (where the expression level is normalized by subtracting the mean and dividing by the standard deviation of the expression levels in the initial set S). The vote of gene g is $v_g=a_g(x_g-b_g)$, with a positive value indicating a vote for class 1 and a negative value indicating a vote for class 2. The total vote $V_1$ for class 1 is obtained by summing the absolute values of the positive votes over the informative genes, while the total vote $V_2$ for class 2 is obtained by summing the absolute values of the negative votes. The votes were summed to determine the winning class, as well as a 'prediction strength' (PS), which is a measure of the margin of victory that ranges from 0 to 1. The prediction strength PS is defined as $PS=(V_{win}-V_{lose})/(V_{win}+V_{lose})$, where $V_{win}$ and $V_{lose}$ are the vote totals for the winning and losing classes. The measure PS reflects the relative margin of victory of the vote. The sample was assigned to the winning class if PS exceeded a predetermined threshold, and is otherwise considered uncertain. Based on prior analysis, a threshold of 0.3 was used for the analyses here.

The appropriate PS threshold depends on the number n of genes in the predictor, because the PS is a sum of n variables corresponding to the individual genes, and thus its fluctuation for random input data scales inversely with $\sqrt{n}$. The analyses described here concern predictors with n=50 genes. The PS threshold of 0.3 was selected based on prior experiments involving classification with 50-gene predictors of the NCI-60 panel of cell lines and normal kidney vs. renal carcinoma comparisons; incorrect predictions in both cases always had PS<0.3. In addition, computer simulations show that comparable random data has less than a 5% chance of yielding a PS>0.3. In fact, the choice of PS threshold has only a minor effect on the results reported here. Eliminating entirely the use of the PS threshold would have resulted in only three incorrect predictions from a total of 72.

The third issue was how to test the validity of class predictors. A two-step procedure was employed. The accuracy of the predictors was first tested by cross-validation on the initial data set. Briefly, one withholds a sample, builds a predictor de novo based only on the remaining samples, and predicts the class of the withheld sample. The process is repeated for each sample, and the cumulative error rate is calculated. One then builds a final predictor based on the initial dataset and assesses its accuracy on an independent set of samples.

This approach was applied to the 38 acute leukemia samples, using the 50 most closely correlated genes as the informative genes. In cross-validation, 36 of the 38 samples were assigned as either AML or ALL and the remaining two samples were uncertain (PS<0.3). In cross-validation, the entire prediction process is repeated from scratch with 37 of the 38 samples. This includes identifying the 50 informative genes to be used in the predictor and defining the parameters for the weighted voting. All 36 predictions agreed with the patients' clinical diagnosis (Table 4).

TABLE 4

| Number of Samples | Source | Method | Strong Predictions | Prediction Accuracy |
|---|---|---|---|---|
| 38 | marrow | cross-validation | 36/38 | 100% |
| 34 | marrow/blood | independent test | 29/34 | 100% |

The accuracy of ALL/AML prediction was 100% both in cross-validation of the initial dataset, and in independent testing of a second dataset. Strong predictions (PS>0.3) were made for the majority of cases; for 2 samples in cross-validation and samples in independent testing, no prediction was made because PS fell below 0.3.

The predictor was then applied to an independent collection of 34 samples from leukemia patients. The specimens consisted of 24 bone marrow and 10 peripheral blood samples as described above. In total, the predictor made strong predictions for 29 of the 34 samples, and the accuracy was 100% (Table 4). The success was notable because the collection included a much broader range of samples, including samples from peripheral blood rather than bone marrow, from childhood AML patients, and from different reference laboratories that employed different sample preparation protocols.

Figure 3A:
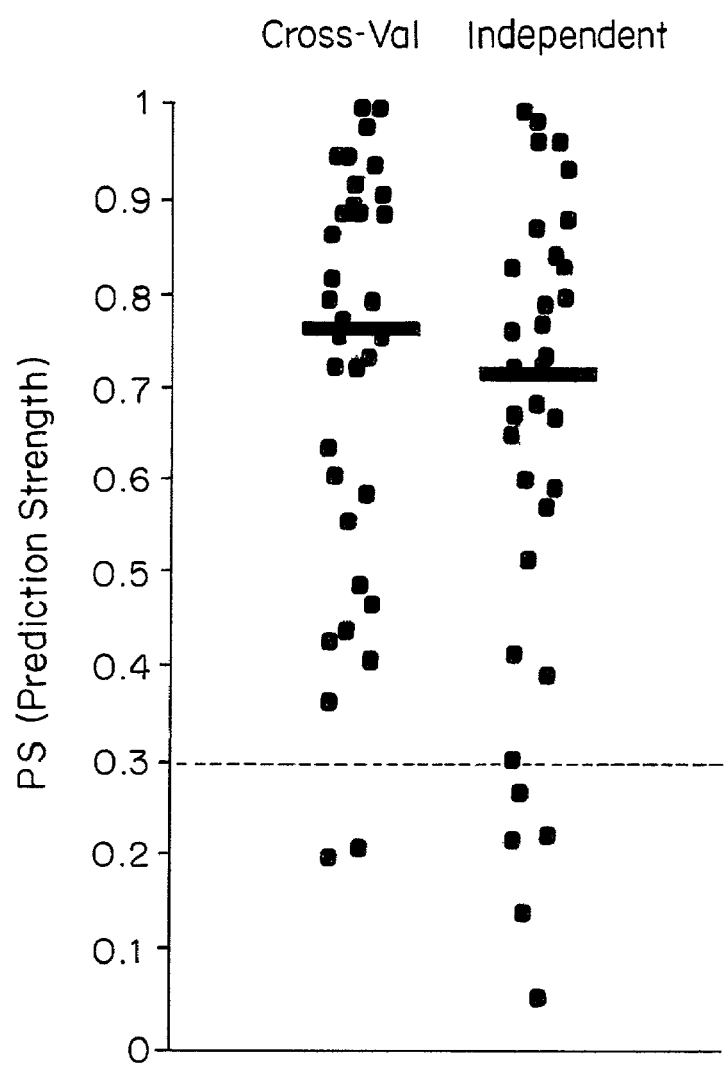
FIGS. 3A–3B show an analysis of ALL and AML samples.

Overall, the prediction strengths were quite high (median PS=0.77 in cross-validation and 0.73 in independent test; FIG. 3A). It was noted that the average prediction strength was somewhat lower for samples from one laboratory that used a very different protocol for sample preparation. This suggests that clinical implementation of such an approach should include standardization of sample preparation.

The choice to use 50 informative genes in the predictor was somewhat arbitrary, although well within the total number of genes strongly correlated with the class distinction (FIGS. 2A–B). In fact, the results proved to be quite insensitive to this choice: class predictors based on between 10 and 200 genes were tested and all were found to be 100% accurate, reflecting the strong correlation of genes with the AML-ALL distinction Although the number of genes used had no significant effect on the outcome in this case (median PS for cross-validation ranged from 0.81 to 0.68 over a range of predictors employing 10–200 genes, all with 0% error), it may matter in other instances. One approach is to vary the number of genes used, select the number that maximizes the accuracy rate in cross-validation and then use the resulting model on the independent dataset. In any case, it is recommend that at at least 10 genes be used for two reasons. Class predictors employing a small number of genes may depend too heavily on any one gene and can produce spuriously high prediction strengths (because a large 'margin of victory' can occur by chance due to statistical fluctuation resulting from a small number of genes). In general, the 1% confidence line in neighborhood analysis was also considered to be the upper bound for gene selection.

Figure 3B:
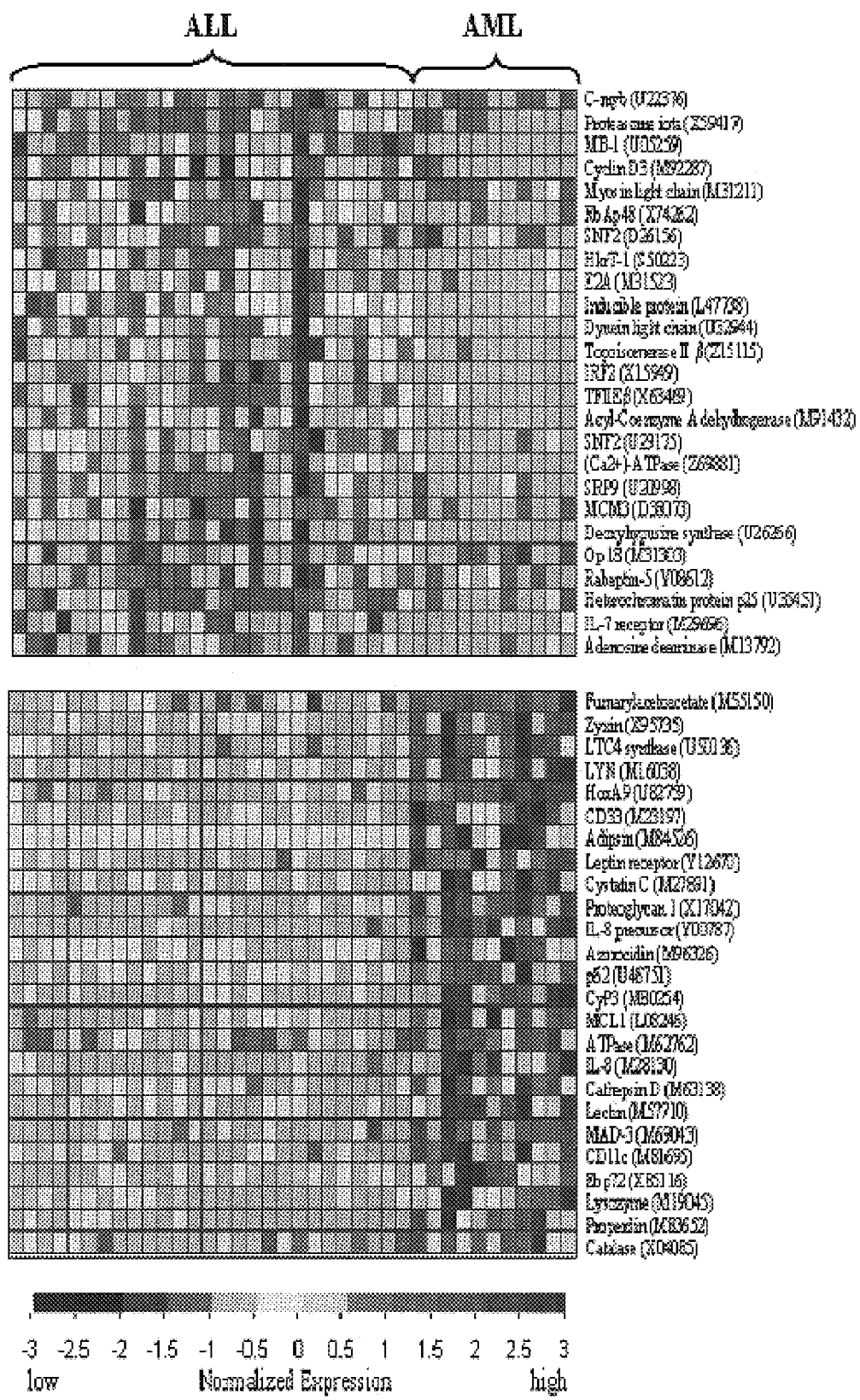

The list of informative genes used in the AML vs. ALL predictor was highly instructive (FIG. 3B). In FIG. 3B, each row corresponds to a gene, with the columns corresponding to expression levels in different samples. Expression levels for each gene are normalized across the samples such that the mean is 0 and the standard deviation is 1. Expression levels greater than the mean are shaded in red, and those below the mean are shaded in blue. The scale indicates standard deviations above or below the mean. The top panel shows genes highly expressed in ALL; the bottom panel shows genes more highly expressed in AML. Note that while these genes as a group appear correlated with class, no single gene is uniformly expressed across the class, illustrating the value of a multi-gene prediction method. For a complete list of gene names, accession numbers and raw expression values, see www.genome.wi.mit.edu/MPR.

Some of these genes, including CD11c, CD33 and MB-1, encode cell surface proteins for which monoclonal antibodies have been previously demonstrated to be useful in distinguishing lymphoid from myeloid lineage cells (P. A. Dinndorf, et al., *Med Pediatr Oncol* 20, 192–200 (1992); P. S. Master, S. J. Richards, J. Kendall, B. E. Roberts, C. S. Scott, *Blut* 59, 221–5 (1989); V. Buccheri, et al., *Blood* 82, 853–7 (1993)). Others provide new markers of acute leukemia subtype. For example, the leptin receptor, originally identified through its role in weight regulation, showed high relative expression in AML. Interestingly, the leptin receptor was recently demonstrated to have anti-apoptotic function in hematopoietic cells (M. Konopleva, et al., *Blood* 93, 1668–76 (1999)). Similarly, the zyxin gene has been previously shown to encode a LIM domain protein important in cell adhesion in fibroblasts, but a role in hematopoiesis has not been previously reported (A. W. Crawford, M. C. Beckerle, *J Biol Chem* 266, 5847–53 (1991)).

It was expected that the genes most useful in AML-ALL class prediction would simply be markers of hematopoietic lineage, and would not necessarily be related to cancer pathogenesis. Surprisingly, many of the genes encode proteins critical for S-phase cell cycle progression (Cyclin D3, Op18 and MCM3), chromatin remodeling (RbAp48, SNF2), transcription (TFIIEβ), cell adhesion (zyxin and CD11c) or are known oncogenes (c-MYB, E2A and HOXA9). In addition, one of the informative genes encodes topoisomerase II, which is known to be the principal target of the anti-leukemic drug etoposide (W. Ross et al., *Cancer Res* 44, 5857–60 (1984)). Together, these data suggest that genes useful for cancer class prediction may also provide insight into cancer pathogenesis and pharmacology.

The approach described above can be applied to any class distinction for which a collection of samples with known answers is available. Importantly, the class distinction could concern a future clinical outcome, such as whether a prostate cancer turned out to be indolent or to grow rapidly, or whether a breast cancer responded to a given chemotherapy. The ability to predict such classes clearly represents an important tool in cancer treatment.

In the case of brain tumors, work described herein demonstrates that the invention was effective at discovering the distinction between two types of tumors (medulloblastoma and glioblastoma). This distinction previously required the expertise of neuropathologists, and few molecular markers are known. Work described herein also demonstrated that the invention successfully predicted the type of brain tumor in cross-validation testing. These studies were performed on RNA extracted from patient biopsies, and the RNA was analyzed on Affymetrix oligonucleotide arrays containing probes for 6817 genes as previously described.

In the case of lymphomas, work described here focused on two types of Non-Hodgkin's lymphoma (folicular lymphoma (FL) and diffuse large B cell lymphoma (DLBCL)). Using RNA derived from patient biopsy materials, the invention was able to discover the FL vs. DLBCL distinction, and was able to diagnose these tumors using class prediction.

Figure 4A:
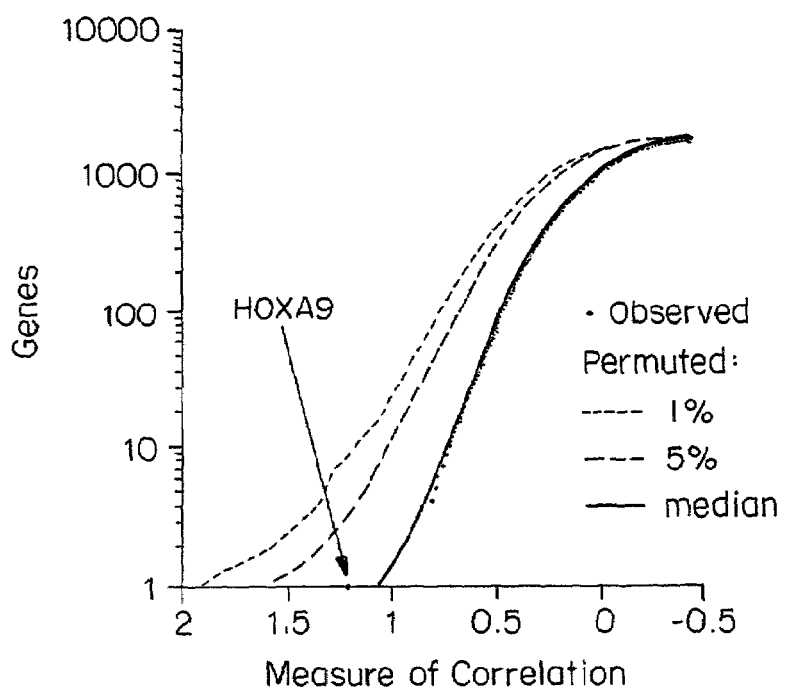
FIGS. 4A–B are a set of graphs showing neighborhood analysis of genes in AML samples from patients with different clinical responses to treatment. Results are shown for 15 AML samples for which long-term clinical follow-up was available, with genes more highly expressed in the treatment failure group in FIG. 4A and genes more highly expressed in the treatment success group in FIG. 4B.
Figure 4B:
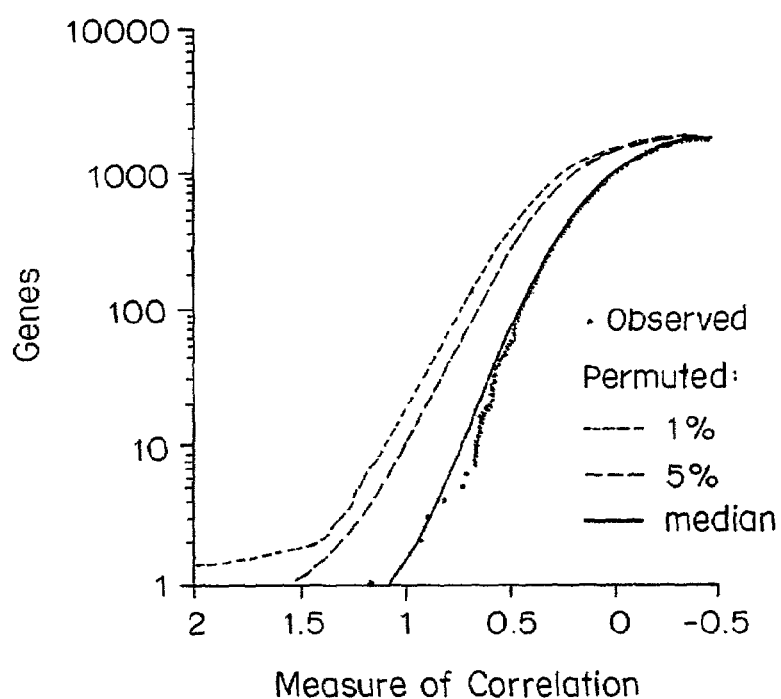

The ability to predict response to chemotherapy among the 15 adult AML patients who had been treated with an anthracycline-cytarabine regimen and for whom long-term clinical follow-up was available was explored. Treatment failure was defined as failure to achieve a complete remission following a standard induction regimen including 3 days of anthracycline and 7 days of cytarabine. Treatment successes were defined as patients in continuous complete remission for a minimum of 3 years. FAB subclass M3 patients were excluded, but samples were otherwise not selected with regard to FAB criteria. Eight patients failed to achieve remission following induction chemotherapy, while the remaining seven patients remain in remission for 46–84 months. In contrast to the situation for the AML-ALL distinction, neighborhood analysis found no striking excess of genes correlated with response to chemotherapy (FIGS. 4A–B). The data fall close to the mean expected from random clusters. Nonetheless, the single most highly correlated gene, HOXA9 (arrow), is biologically related to AML. As might be expected, class predictors employing 10 to 50 genes were not highly accurate in cross-validation. For example, a 10-gene predictor yielded strong predictions (PS>0.3) for only 40% of the samples, and of those, 67% of the predictions were incorrect. Similarly, a 50-gene predictor yielded strong predictions for 27% of the samples, and 75% of these predictions were incorrect.

The lack of a significant excess of correlated genes, however, does not imply that there are no genetic predictors of chemotherapy response: some of the most highly correlated genes could be valid predictors of response, but could fall short of statistical significance due to the small sample size. Accordingly, it is also important to examine these genes for potential biological insight. Intriguingly, the single most highly correlated gene out of the 6817 genes studied (having a nominal significance level of p=0.0001) was the homeobox gene HOXA9, which was overexpressed in patients with treatment failure. HOXA9 is known to be rearranged by the t(7;11)(p15;p15) chromosomal translocation in a rare subset of patients with AML, and these patients tend to have poor outcomes (J. Borrow, et al., *Nat Genet* 12, 159–67 (1996); T. Nakamura, et al., *Nat Genet* 12, 154–8 (1996); S. Y. Huang, et al., *Br J Haematol* 96, 682–7 (1997)). Furthermore, HOXA9 overexpression has been shown to transform myeloid cells in vitro and to cause leukemia in animal models (E. Kroon, et al., *Embo J* 17, 3714–25 (1998)). A general role for HOXA9 expression in predicting AML outcome has not been previously explored.

EXAMPLE 2

Class Discovery

Class prediction presumes that one already has discovered biologically relevant classes. In fact, the initial identification of cancer classes has been slow, typically evolving through years of hypothesis-driven research. Accordingly, the next question was how such classes could be discovered in the first place.

Class discovery entails two key issues: finding clusters and evaluating clusters. The first issue concerns algorithms for clustering tumors by gene expression to identify meaningful biological classes. The second, more challenging issue addresses whether putative classes produced by such clustering algorithms are meaningful—that is, whether they reflect true structure in the data rather than simply random aggregation.

This work began by exploring whether clustering tumors by gene expression readily reveals key classes among acute leukemias. Several mathematical approaches to clustering expression data have been recently reported. (P. T. Spellman et al., *Mol Biol Cell* 9:3273–97 (1998); M. B. Eisen et al., *Proc Natl Acad Sci USA* 95:14863–68 (1998); V. R. Iyer et al., *Science* 283:83–87 (1999); Tavazoie et al., *Nat Genet* 22:181–5 (1999)). In the work described herein, a technique called Self-Organizing Maps (SOMs), which is particularly well suited to the task of identifying a small number of prominent classes in a dataset was used. (P. Tamayo, et al., *Proc Natl Acad Sci USA* 96, 2907–2912 (1999)).

In this approach, the user specifies the number of clusters to be identified. The SOM finds an optimal set of 'centroids' around which the data points appear to aggregate. It then partitions the dataset, with each centroid defining a cluster consisting of the data points nearest to it. In addition to specifying the desired number of clusters, the user can also specify any desired 'geometry' relating the clusters.

Figure 5A:
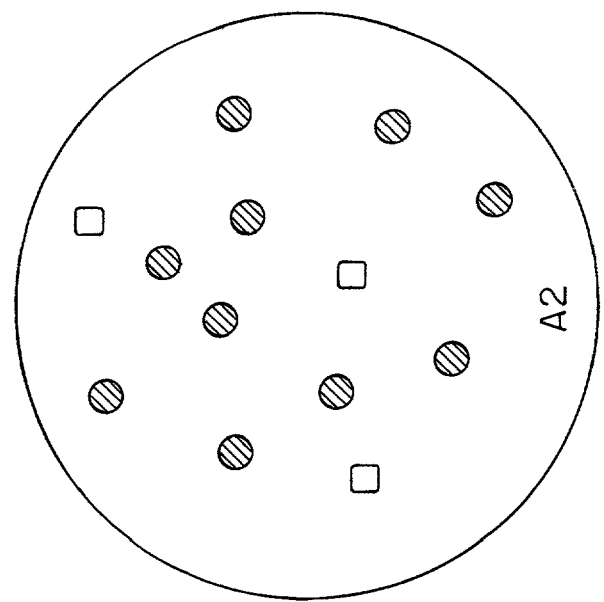
FIGS. 5A–5D illustrate class discovery of ALL and AML classes.
Figure 5A:
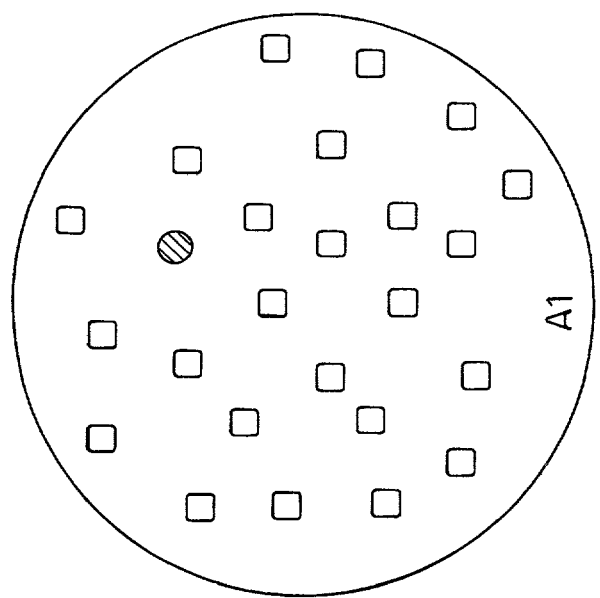

As described herein, a 2-cluster SOM was applied to automatically group the 38 initial leukemia samples into two classes on the basis of the expression pattern of all 6817 genes. The SOM was constructed using GENECLUSTER software (P. Tamayo, et al., *Proc Natl Acad Sci USA* 96, 2907–2912 (1999)). The clustering process began with the expression levels for all 6,817 genes. The first step eliminated genes showing no significant change in expression across the samples (defined as less than five-fold difference between minimum and maximum). A total of 3,062 of the 6,817 genes passed this criteria. The normalized values for these genes were then used to construct the SOM. The clusters were first evaluated by comparing them to the known AML-ALL classes (FIG. 5A). Each of the 38 samples is thereby placed into one of two clusters on the basis of patterns of gene expression for the 6817 genes assayed in each sample. Note that cluster Al contains the majority of ALL samples (grey squares), and cluster A2 contains the majority of AML samples (black circles). The SOM paralleled the known classes closely: class Al contained mostly ALL (24 of 25 samples) and class A2 contained mostly AML (10 of 13 samples). The SOM was thus quite effective, albeit not perfect, at automatically discovering the two types of leukemia.

The question of how one would evaluate such clusters in a discovery setting, in which the 'right' answer was not already known, was then considered. This work proposes that class discovery is best evaluated through class prediction. If putative classes reflect true underlying structure, then a class predictor based on them should perform well. If not, the predictor should perform poorly. The performance of the predictor can be measured in both cross-validation and on independent data.

To test this hypothesis, the clusters A1 and A2 were evaluated. Predictors were constructed to assign new samples as 'type A1' or 'type A2'. The predictors were first tested by cross-validation. Predictors using a wide range of different numbers of informative genes were found to perform well. For example, a 20-gene predictor gave 34 accurate predictions with high prediction strength, 1 error and 3 uncertains. For testing putative clusters, class predictors were constructed with various number of genes (ranging from 10 to 100), and the one with the highest cross-validation accuracy rate (in this case, 20 genes) was selected. The process was employed both for the SOM-derived clusters and for random clusters to which they were compared. Interestingly, the one 'error' was the prediction of the sole AML sample in class A1 to class A2, and two of the three uncertains were ALL samples in class A2. The cross validation thus not only showed high accuracy, but actually refined the SOM-defined classes: with one exception, the subset of samples accurately classified in cross validation were those perfectly divided by the SOM into ALL and AML classes. The results suggest an iterative procedure for refining the definition of clusters, in which a SOM is used to cluster the data, a predictor is constructed, and samples that fail to be correctly predicted in cross-validation are removed. A related approach would be to represent each cluster only as the subset of points lying near the centroid of the cluster.

Figure 5B:
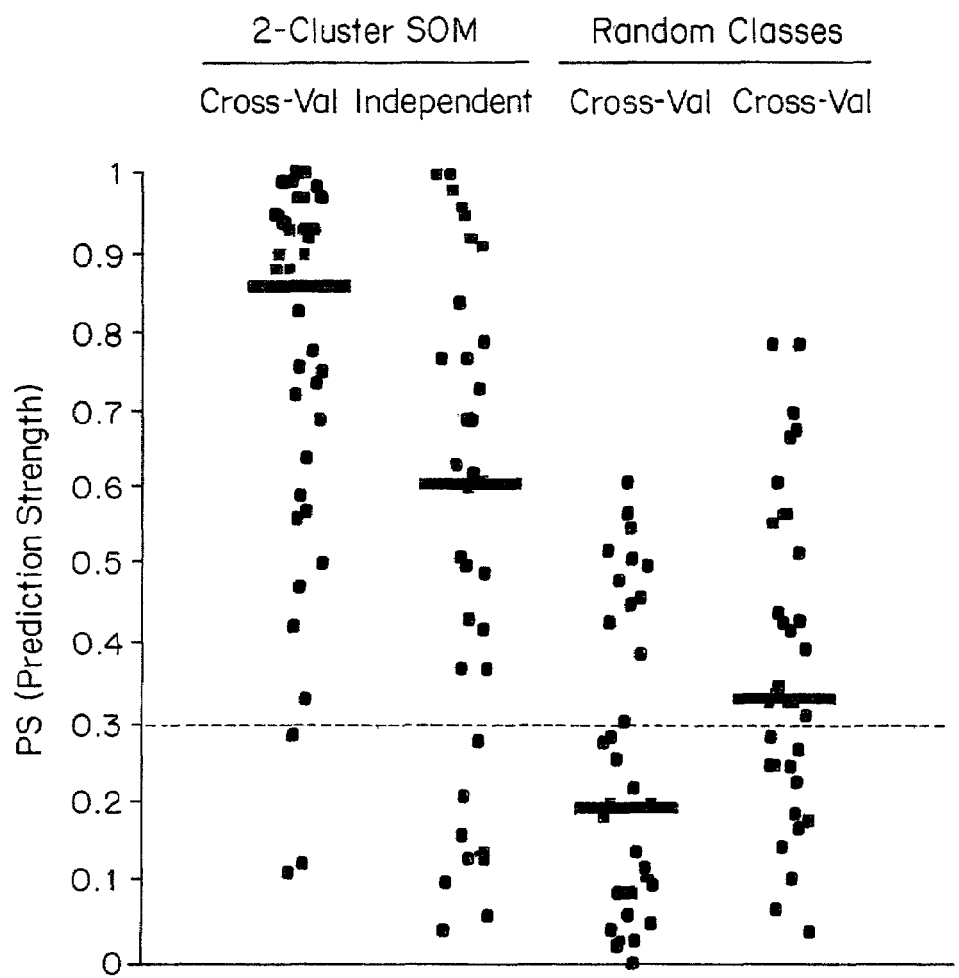

The class predictor of A1–A2 distinction was then tested on the independent dataset. In the general case of class discovery, predictors for novel classes cannot be assessed for 'accuracy' on new samples, because the 'right' way to classify the independent samples is not known. Instead, however, one can assess whether the new samples are assigned a high prediction strength. High prediction strengths indicate that the structure seen in the initial dataset is also seen in the independent dataset. In fact, the prediction strengths were quite high: the median PS was 0.61 and 74% of samples were above threshold (FIG. 5B).

To further assess these results, the same analyses were performed with random clusters. Such clusters consistently yielded predictors with poor accuracy in cross-validation and low prediction strength on the independent data set (FIG. 5B). In these cases, the PS scores are much lower (median PS=0.20 and 0.34, respectively) and approximately half of the samples fall below the threshold for prediction (PS=0.3). A total of 100 such random predictors were examined, to calculate the distribution of median PS scores to evaluate statistical the significance of the predictor for A1–A2. Various statistical methods can be used to compare the predictors derived from the SOM-derived clusters with predictors derived from random classes. The simple approach of analyzing median prediction strengths was used herein. Specifically, 100 predictors were constructed corresponding to random classes of comparable size, and the distribution of PS was determined for each predictor. The distribution of the median PS for these 100 random predictors was then considered. The performance for the actual predictor was then compared to this distribution, to obtain empirical significance levels. The observed median PS in the initial data set was 0.86, which exceeded the median PS for all 100 random predictors; the empirical significance level was thus <1%. The observed median PS for the independent data set was 0.61, which exceed the median PS for all but four of the 100 random permutations; the empirical significance level was thus 4%. Based on such analysis, the A1–A2 distinction can be readily seen to be meaningful, rather than simply a statistical artifact of the initial dataset. The results thus show that the AML-ALL distinction could have been automatically discovered and confirmed without prior biological knowledge.

Figure 5C:
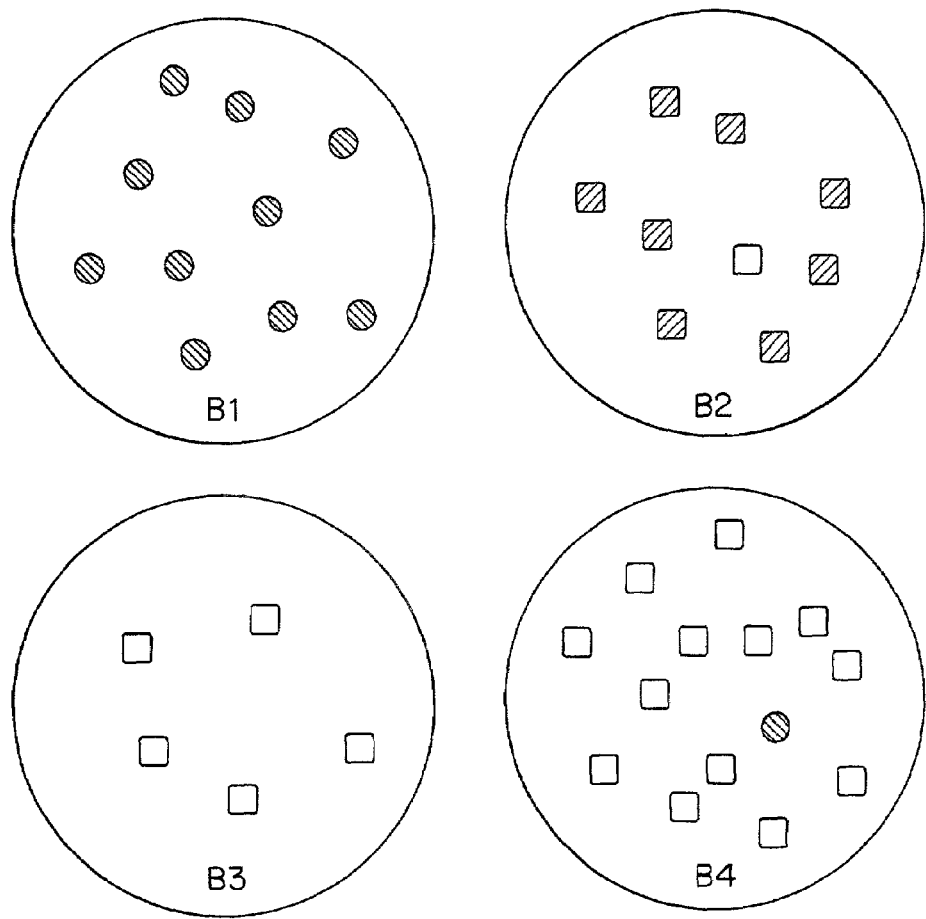

The class discovery was then extended by searching for finer subclasses of the leukemias. A 2×2 SOM was used to divide the samples into four clusters (denoted B1–B4). Immunophenotyping data was subsequently obtained on the samples, and it was found that the four classes largely corresponded to AML, T-lineage ALL, B-lineage ALL and B-lineage ALL, respectively (FIG. 5C). Note that class B1 is exclusively AML, class B2 contains all 8 T-ALLs, and classes B3 and B4 contain the majority of of B-ALL samples. The 4-cluster SOM thus divided the samples along another key biological distinction.

Figure 5D:
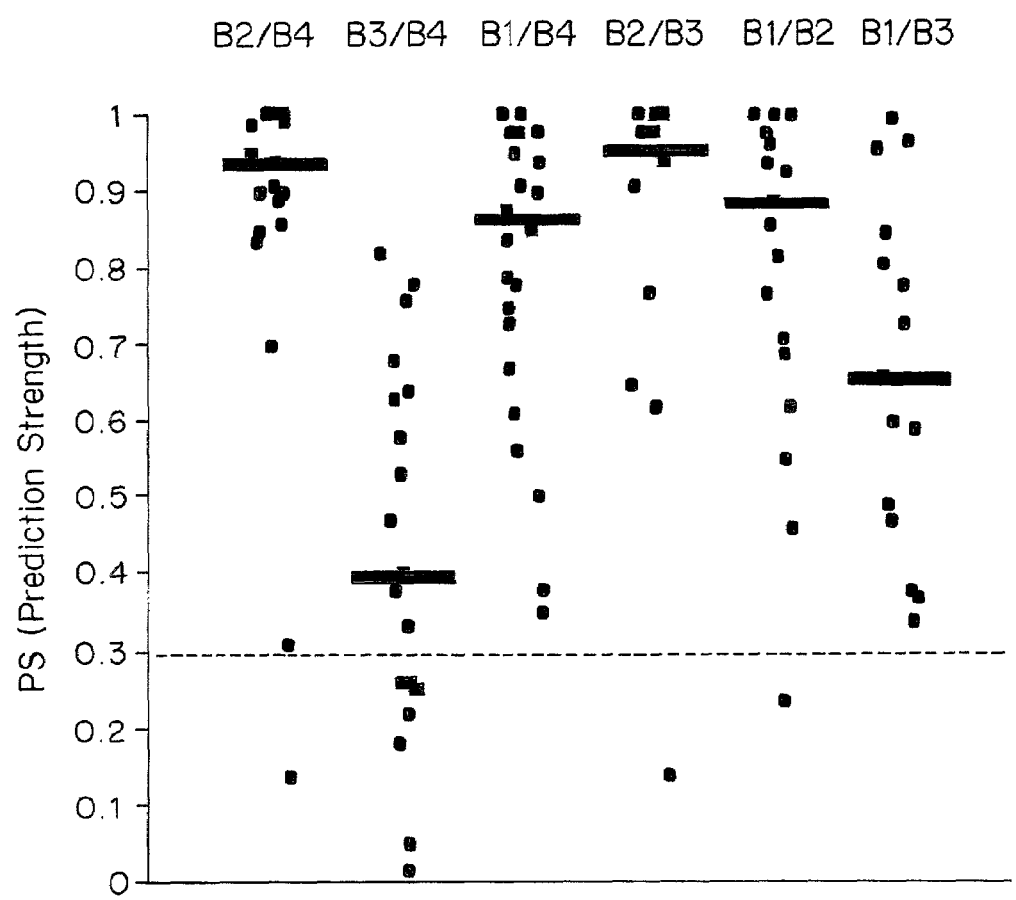

These classes were evaluated again by constructing class predictors. Various approaches can be used to test classes $C_1$, $C_2$, . . . , $C_n$ arising from a multi-node SOM. One can construct predictors to distinguish each pair of classes ($C_i$ vs. $C_j$) or to distinguish each class for the complement of the class ($C_i$ vs. not $C_j$). It is straightforward to use both approaches in cross-validation (to measure accuracy in the first approach, one can restrict attention only to samples in $C_i$ and $C_j$). Subtler issues concerning statistical power arise in testing predictors for a large number of classes on an independent dataset. For the analysis described herein, the pairwise approach ($C_i$ vs. $C_j$) was used in both cross-validation and independent testing. The four classes could be distinguished from one another, with the exception of B3 vs. B4 (FIG. 5D). These two classes could not be easily distinguished from one another, consistent with their both containing-primarily B-ALL samples, and suggesting that B3 and B4 might best be merged into a single class. The prediction tests thus confirmed the distinctions corresponding to AML, B-ALL and T-ALL, and suggested that it may be appropriate to merge classes B3 and B4, composed primarily of B-lineage ALL.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of assigning a sample to a known class, comprising the steps of:
   a. determining a weighted vote for one or more informative genes for the known class in said sample in accordance with a model built with a weighted voting scheme, wherein the magnitude of each vote depends on the expression level of the one or more informative genes in said sample and on the degree of correlation of the one or more informative genes' expression with class distinction;
   b. summing the votes to determine a winning class and a prediction strength;
   c. assigning said sample to the winning class, which winning class is a known class, if the prediction strength is greater than a prediction strength threshold; and
   d. providing an output indicating assignment of said sample to the winning class, wherein the known class is a cancer disease class selected from any of Acute Lymphoblastic Leukemia (ALL), Acute Myeloid Leukemia (AML), glioblastoma, medulloblastoma, folicular lymphoma, or diffuse large B cell lymphoma.

2. The method of claim 1, wherein the cancer disease class is Acute Lymphoblastic Leukemia (ALL) or Acute Myeloid Leukemia (AML).

3. The method of claim 1, wherein the prediction strength is determined by:

$$(V_{win} - V_{lose})/(V_{win} + V_{lose}),$$

wherein $V_{win}$ and $V_{lose}$ are the vote totals for one or more winning and losing classes, respectively.

4. The method of claim 3, wherein the cancer disease class is Acute Lymphoblastic Leukemia (ALL) or Acute Myeloid Leukemia (AML).

5. The method of claim 3, wherein the number of informative genes used in the weighted voting scheme is at least 50.

6. The method of claim 5, wherein the cancer disease class is glioblastoma or medulloblastoma.

7. The method of claim 5, wherein the cancer disease class is folicular lymphoma or diffuse large B cell lymphoma.

8. The method of claim 5, wherein the cancer disease class is Acute Lymphoblastic Leukemia (ALL) or Acute Myeloid Leukemia (AML).

9. The method of claim 8, wherein the informative genes encode proteins selected from the group consisting of: c-myb, MB-1, cyclinD3, Rb Ap48, SNF2, E2A, topoisomerase II β, TFIIEβ, MCM3, Op 18, zyxin, HoxA9, CD33, and CD11c.

10. The method of claim 8, wherein the informative genes are markers of hematopoietic lineage.

11. The method of claim 1, wherein the output comprises an output assembly.

12. The method of claim 11, wherein the output assembly comprises a graphical representation.

* * * * *